(12) United States Patent
Kashmiri et al.

(10) Patent No.: US 7,915,396 B2
(45) Date of Patent: Mar. 29, 2011

(54) NUCLEIC ACID MOLECULES ENCODING MINIMALLY IMMUNOGENIC VARIANTS OF SDR-GRAFTED HUMANIZED ANTIBODY CC49

(75) Inventors: Syed V. S. Kashmiri, Gaithersburg, MD (US); Jeffrey Schlom, Potomac, MD (US); Eduardo A. Padlan, Kensington, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/544,978

(22) Filed: Aug. 20, 2009

(65) Prior Publication Data

US 2009/0311780 A1 Dec. 17, 2009

Related U.S. Application Data

(62) Division of application No. 10/570,220, filed as application No. PCT/US2004/028004 on Aug. 27, 2004, now Pat. No. 7,589,181.

(60) Provisional application No. 60/498,903, filed on Aug. 29, 2003.

(51) Int. Cl.
| | |
|---|---|
| *C07H 21/04* | (2006.01) |
| *C12P 21/04* | (2006.01) |
| *C12N 7/00* | (2006.01) |
| *C12N 15/00* | (2006.01) |
| *A61K 39/395* | (2006.01) |
| *C07K 16/00* | (2006.01) |
| *C12P 21/08* | (2006.01) |

(52) U.S. Cl. ............... 536/23.53; 424/133.1; 424/141.1; 424/155.1; 424/178.1; 435/69.6; 435/235.1; 435/320.1; 435/328; 530/387.3; 530/388.1; 530/388.8; 530/391.3

(58) Field of Classification Search ........................ None
See application file for complete search history.

(56) References Cited

U.S. PATENT DOCUMENTS

| | | | |
|---|---|---|---|
| 4,816,567 | A | 3/1989 | Cabilly et al. |
| 5,472,693 | A | 12/1995 | Gourlie et al. |
| 5,482,040 | A | 1/1996 | Martin, Jr. |
| 5,512,443 | A | 4/1996 | Schlom et al. |
| 5,534,254 | A | 7/1996 | Huston et al. |
| 5,585,089 | A | 12/1996 | Queen et al. |
| 5,618,920 | A * | 4/1997 | Robinson et al. |
| 5,688,657 | A | 11/1997 | Tsang et al. |
| 5,976,531 | A | 11/1999 | Mezes et al. |
| 5,976,845 | A | 11/1999 | Mezes et al. |
| 5,994,511 | A | 11/1999 | Lowman et al. |
| 6,054,297 | A | 4/2000 | Carter et al. |
| 6,180,370 | B1 | 1/2001 | Queen et al. |
| 6,333,405 | B1 | 12/2001 | Anderson et al. |
| 6,495,137 | B1 | 12/2002 | Mezes et al. |

FOREIGN PATENT DOCUMENTS

| | | |
|---|---|---|
| CA | 2131355 | 3/1996 |
| CA | 2068593 | 7/2003 |
| EP | 0239400 | 9/1987 |
| EP | 0365997 | 5/1990 |
| WO | WO 89/00692 | 1/1989 |
| WO | WO 89/01783 | 3/1989 |
| WO | WO 90/04410 | 5/1990 |
| WO | WO 91/00295 | 1/1991 |
| WO | WO 93/12231 | 6/1993 |
| WO | WO 96/13594 | 5/1996 |
| WO | WO 97/26010 | 7/1997 |
| WO | WO 98/18809 | 5/1998 |
| WO | WO 99/43816 | 9/1999 |
| WO | WO 00/26394 | 5/2000 |
| WO | WO 2004/003155 | 1/2004 |

OTHER PUBLICATIONS

Fundamental Immunology, William E. Paul, M.D. ed., 3rd ed., p. 242, 1993.*
Abergel et al., "Crystallographic Studies and Primary Structure of the Antitumor Monoclonal CC49 Fab'," *Proteins: Structure, Function, and Genetics* 17:438-443, 1993.
Berzofsky et al., p. 242, *Fundamental Immunology*, Paul (Ed.) Raven Press, NY, 1993.
Colcher et al., "Radioimmunolocalization of Human Carcinoma Xenografts with B72.3 Second Generation Monoclonal Antibodies," *Cancer Research* 48:4597-4603, 1988. De Pascalis et al., "Generation of minimally immunogenic high affinity variants of humanized anti-carcinoma antibody HuCC49V10 by in vitro affinity maturation," *Proceedings of the American Association for Cancer Research*, 44(2):1115-1116, 2003.
De Pascalis et al., "In Vitro Affinity Maturation of a Specificity-Determining Region-Grafted Humanized Anticarcinoma Antibody: Isolation and Characterization of Minimally Immunogenic High-Affinity Variants," *Clinical Cancer Research*, 9:5521-5531, 2003.
Divgi et al., "Clinical Comparison of Radiolocalization of Two Monoclonal Antibodies (mAbs) Against the TAG-72 Antigen," *Nucl. Med. Biol.* 21(1):9-15, 1994.
Gonzales et al., "Minimizing immunogenicity of the SDR-grafted humanized antibody CC49 by genetic manipulation of the framework residues," *Molecular Immunology*, 40(6):337-349, 2003.
Gonzales et al., "Reducing the potential immunogenicity of humanized CC49 by genetic manipulation of framework residues," *Proceedings of the American Association for Cancer Research*, 44:1118, 2003.

(Continued)

*Primary Examiner* — David J. Blanchard
(74) *Attorney, Agent, or Firm* — Klarquist Sparkman, LLP

(57) ABSTRACT

Humanized anti-TAG-72 CC49 monoclonal antibodies are disclosed herein. The antibodies include a light chain Complementarity Determining Region (L-CDR)1, a L-CDR2, and a L-CDR3; and a heavy chain Complementarity Determining Region (H-CDR)1, a H-CDR2, and a H-CDR3 from humanized antibody HuCC49V10. The L-CDR1, L-CDR2, L-CDR3 are within a HuCC49V10 light chain framework region that includes the corresponding amino acid from LEN at position 5, 19, 21, and 106 in the light chain. The H-CDR1, H-CDR2, and H-CDR3 are within a heavy chain HuCC49V10 framework comprising a human 21/28' CL residue at positions 20, 38, 48, 66, 67, 69, and 80 in the heavy chain. These humanized CC49 antibodies retain binding affinity for TAG-72 and have reduced immunogenicity, as compared to a parental HuCC49V10 antibody. Methods are disclosed herein for using these antibodies in the treatment or diagnosis of a tumor, such as a carcinoma, expressing TAG-72.

14 Claims, 9 Drawing Sheets

OTHER PUBLICATIONS

Hakimi et al., "Reduced immunogenicity and improved pharmacokinetics of humanized anti-Tac in cynomolgus monkeys," *J. Immunol.* 147:1352-1359, 1991.

Hand et al., "Potential for Recombinant Immunoglobulin Constructs in the Management of Carcinoma," *Cancer Supplement* 73(3):1105-1113, 1994.

Iwahashi et al., "CDR Substitutions of a Humanized Monoclonal Antibody (CC49): Contributions of Individual CDRs to Antigen Binding and Immunogenicity," *Molecular Immunology* 36:1079-1091, 1999.

Johnson et al., "Analysis of a Human Tumor-associated Glycoprotein (TAG-72) Identified by Monoclonal Antibody B72.3," *Cancer Research* 46:850-857, 1986.

Jones et al., "Replacing the Complementarity-determining Regions in a Human Antibody with those from a Mouse," *Nature* 321:522-525, 1986.

Kashmiri et al., Chapter 21 in *Methods in Molecular Biology, vol. 248: Antibody Engineering: Methods and Protocols*, p. 361-376; Lo (ed.), Humana Press, Inc., Tolowa, NJ, 2003.

Kashmiri et al., "Development of a minimally immunogenic variant of humanized anti-carcinoma monoclonal antibody CC49," *Crit. Rev. Oncol. Hematol.* 38:3-16, 2001.

Kashmiri et al, "Generation, Characterization, and in Vivo Studies of Humanized Anticarcinoma Antibody CC49," *Hybridoma* 14(5):461-473, 1995.

Kashmiri et al., "SDR grafting—a new approach to antibody humanization," *Methods*, 36:25-34, 2005.

Mulligan et al., "Phase I Study of Intravenous $^{177}$Lu-labeled CC49 Murine Monoclonal Antibody in Patients with Advanced Adenocarcinoma," *Clinical Cancer Research* 1:1447-1454, 1995.

Muraro et al., "Generation and Characterization of B72.3 Second Generation Monoclonal Antibodies Reactive with the Tumor-associated Glycoprotein 72 Antigen," *Cancer Research* 48:4588-4596, 1988.

Padlan, "A Possible Procedure for Reducing the Immunogenicity of Antibody Variable Domains while Preserving their Ligand-binding Properties," *Molecular Immunology* 28(4/5):489-498, 1991.

Padlan, "Anatomy of the antibody molecule," *Mol. Immunol.* 31:169-217, 1994.

Padlan et al., "Identification of Specificity-determining Residues in Antibodies," *The FASEB Journal* 9:133-139, 1995.

Riechman et al., "Reshaping human antibodies for therapy," *Nature (London)* 332:323-327, 1988.

Rixon et al., "Preferential Use of a H Chain V Region in Antitumor-associated Glycoprotein-72 Monoclonal Antibodies," *The Journal of Immunology* 151(11):6559-6568, 1993.

Rudikoff et al., "Single amino acid substitution altering antigen-binding specificity," *PNAS* 79(6):1979-1983, 1982.

Saldanha et al., "A single backmutation in the human kIV framework of a previously unsuccessfully humanized antibody restores the binding activity and increases the secretion in cos cells," *Mol. Immunol.* 36:709-719, 1999.

Schier et al., "Isolation of picomolar affinity anti-c-erbB-2 single-chain Fv by molecular evolution of the complementarity determining regions in the center of the antibody binding site," *J. Mol. Biol.* 263:551-567, 1996.

Sha et al., "A Heavy-chain Grafted Antibody that Recognizes the Tumor-associated TAG72 Antigen," *Cancer Biotherapy* 9(4):341-349, 1994.

Sharkey et al., "Evaluation of a complementarity-determining region-grafted (humanized) anti-carcinoembryonic antigen monoclonal antibody in preclinical and clinical studies," *Cancer Res.* 55:5935s-5945s, 1995.

Slavin-Chiorini et al., "A CDR-grafted (humanized) domain-deleted antitumor antibody," *Cancer Biother. Radiopharm.* 12:305-316, 1997.

Slavin-Chiorini et al., "Biological Properties of Chimeric Domain-deleted Anticarcinoma Immunoglobulins," *Cancer Research (Supplement)* 55:5957s-5967s, 1995.

Tamura et al., "Structural Correlates of an Anticarcinoma Antibody: Identification of Specificity-determining Residues (SDRs) and Development of a Minimally Immunogenic Antibody Variant by Retention of SDRs Only," *Journal of Immunology* 164(3):1432-1441, 2000.

Wu et al., "Humanization of a murine monoclonal antibody by simultaneous optimization of framework and CDR residues," *J. Mol. Biol.* 294:151-162, 1999.

Xiang et al., "The Tyrosine Residue at Position 97 in the $V_H$ CDR3 Region of a Mouse/Human Chimeric Anti-Colorectal Carcinoma Antibody Contributes Hydrogen Bonding to the TAG72 Antigen," *Cancer Biotherapy* 8(3):253-262, 1993.

Xiang et al., "Complementarity Determining Region Residues Aspartic Acid at H55, Serine at H95 and Tyrosines at H97 and L96 Play Important Roles in the B72.3 Antibody-TAG72 Antigen Interaction," *Protein Engineering* 9(6):539-543, 1996.

Xiang et al., "Light-chain framework region residue Tyr71 of chimeric B72.3 antibody plays an important role in influencing the TAG72 antigen binding," *Protein Eng.* 12:417-421, 1999.

International Search Report issued on Apr. 15, 2005, for PCT Patent Application No. PCT/US2004/028004.

* cited by examiner

FIG. 8

Light Chain

| CDR1 | 24 | 25 | 26 | 27 | a | b | c | d | e | f | 28 | 29 | 30 | 31 | 32 | 33 | 34 |
|---|---|---|---|---|---|---|---|---|---|---|---|---|---|---|---|---|---|
| CC49/HuCC49 | Lys | Ser | Ser | Gln | Ser | Leu | Leu | Tyr | Ser | Gly | Asn | Gln | Lys | Asn | Tyr | Leu | Ala |
| LEN | Lys | Ser | Ser | Gln | Ser | *Val* | Leu | Tyr | Ser | *Ser* | Asn | *Ser* | Lys | Asn | Tyr | Leu | Ala |

| CDR2 | 50 | 51 | 52 | 53 | 54 | 55 | 56 |
|---|---|---|---|---|---|---|---|
| CC49/HuCC49 | Trp | Ala | Ser | Ala | Arg | Glu | Ser |
| LEN | Trp | Ala | Ser | *Thr* | Arg | Glu | Ser |

| CDR3 | 89 | 90 | 91 | 92 | 93 | 94 | 95 | 96 | 97 |
|---|---|---|---|---|---|---|---|---|---|
| CC49/HuCC49 | Gln | Gln | Tyr | Tyr | Ser | Tyr | Pro | Leu | Thr |
| LEN | Gln | Gln | Tyr | Tyr | Ser | *Thr* | Pro | *Tyr* | *Ser* |

Heavy Chain

| CDR1 | 31 | 32 | 33 | 34 | 35 |
|---|---|---|---|---|---|
| CC49/HuCC49 | Asp | His | Ala | Ile | His |
| 21/28'CL | *Ser* | *Tyr* | Ala | *Met* | His |

| CDR2 | 50 | 51 | 52 | a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| CC49/HuCC49 | Tyr | Phe | Ser | Pro | Gly | Asn | Asp | Asp | Phe | Lys | Tyr | Asn | Glu | Arg | Phe | Lys | Gly |
| 21/28'CL | *Trp* | *Ile* | *Asn* | *Ala* | Gly | Asn | *Gly* | *Asn* | *Thr* | Lys | Tyr | *Ser* | *Gln* | Lys | Phe | *Gln* | Gly |

| CDR3 | 95 | 96 | 97 | 98 | 99 | 100 | a | b | 101 | 102 |
|---|---|---|---|---|---|---|---|---|---|---|
| CC49/HuCC49 | Ser | Leu | Asn | Met | Ala | - | - | - | - | Tyr |
| 21/28'CL | *Gly* | *Gly* | *Tyr* | *Tyr* | *Gly* | *Ser* | *Gly* | *Ser* | *Asn* | Tyr |

FIG. 9A

Light Chain

| CDR1 | | 24 | 25 | 26 | 27 | a | b | c | d | e | f | 28 | 29 | 30 | 31 | 32 | 33 | 34 |
|---|---|---|---|---|---|---|---|---|---|---|---|---|---|---|---|---|---|---|
| CC49/HuCC49 | | Lys | Ser | Ser | Gln | Ser | Leu | Leu | Tyr | Ser | Gly | Asn | Gln | Lys | Asn | Tyr | Leu | Ala |
| LEN | | Lys | Ser | Ser | Gln | Ser | *Val* | Leu | Tyr | Ser | *Ser* | Asn | *Ser* | Lys | Asn | Tyr | Leu | Ala |

| CDR2 | | 50 | 51 | 52 | 53 | 54 | 55 | 56 |
|---|---|---|---|---|---|---|---|---|
| CC49/HuCC49 | | Trp | Ala | Ser | Ala | Arg | Glu | Ser |
| LEN | | Trp | Ala | Ser | *Thr* | Arg | Glu | Ser |

| CDR3 | | 89 | 90 | 91 | 92 | 93 | 94 | 95 | 96 | 97 |
|---|---|---|---|---|---|---|---|---|---|---|
| CC49/HuCC49 | | Gln | Gln | Tyr | Tyr | Ser | Tyr | Pro | Leu | Thr |
| LEN | | Gln | Gln | Tyr | Tyr | Ser | *Thr* | Pro | *Tyr* | *Ser* |

FIG. 9B

Heavy Chain

| CDR1 | | 31 | 32 | 33 | 34 | 35 |
|---|---|---|---|---|---|---|
| CC49/HuCC49 | | Asp | His | Ala | Ile | His |
| 21/28'CL | | *Ser* | *Tyr* | Ala | *Met* | His |

| CDR2 | | 50 | 51 | 52 | a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| CC49/HuCC49 | | Tyr | Phe | Ser | Pro | Gly | Asn | Asp | Asp | Phe | Lys | Tyr | Asn | Glu | Arg | Phe | Lys | Gly |
| 21/28'CL | | *Trp* | *Ile* | *Asn* | *Ala* | Gly | Asn | *Gly* | *Asn* | *Thr* | Lys | Tyr | *Ser* | *Gln* | *Lys* | Phe | *Gln* | Gly |

| CDR3 | | 95 | 96 | 97 | 98 | 99 | 100 | a | b | 101 | 102 |
|---|---|---|---|---|---|---|---|---|---|---|---|
| CC49/HuCC49 | | Ser | Leu | Asn | Met | Ala | - | - | - | - | Tyr |
| 21/28'CL | | *Gly* | *Gly* | *Tyr* | *Tyr* | *Gly* | *Ser* | *Gly* | *Ser* | *Asn* | Tyr |

```
                        SEQUENCE LISTING

<160> NUMBER OF SEQ ID NOS: 82

<210> SEQ ID NO 1
<211> LENGTH: 23
<212> TYPE: PRT
<213> ORGANISM: Artificial sequence
<220> FEATURE:
<223> OTHER INFORMATION: light chain framework region 1 of the humanized
      antibody HuCC49V10

<400> SEQUENCE: 1

Asp Ile Val Met Ser Gln Ser Pro Asp Ser Leu Ala Val Ser Leu Gly
1               5                   10                  15

Glu Arg Val Thr Leu Asn Cys
            20

<210> SEQ ID NO 2
<211> LENGTH: 15
<212> TYPE: PRT
<213> ORGANISM: Artificial Sequence
<220> FEATURE:
<223> OTHER INFORMATION: light chain framework region 2 of the humanized
      antibody HuCC49V10

<400> SEQUENCE: 2

Trp Tyr Gln Gln Lys Pro Gly Gln Ser Pro Lys Leu Leu Ile Tyr
1               5                   10                  15

<210> SEQ ID NO 3
<211> LENGTH: 32
<212> TYPE: PRT
<213> ORGANISM: Artificial Sequence
<220> FEATURE:
<223> OTHER INFORMATION: light chain framework region 3 of the humanized
      antibody HuCC49V10

<400> SEQUENCE: 3

Gly Val Pro Asp Arg Phe Ser Gly Ser Gly Ser Gly Thr Asp Phe Thr
1               5                   10                  15

Leu Thr Ile Ser Ser Val Gln Ala Glu Asp Val Ala Val Tyr Tyr Cys
            20                  25                  30
```

```
<210> SEQ ID NO 4
<211> LENGTH: 10
<212> TYPE: PRT
<213> ORGANISM: Artificial Sequence
<220> FEATURE:
<223> OTHER INFORMATION: light chain framework region 4 of the humanized
      antibody HuCC49V10

<400> SEQUENCE: 4

Phe Gly Ala Gly Thr Lys Leu Glu Leu Lys
1               5                   10

<210> SEQ ID NO 5
<211> LENGTH: 30
<212> TYPE: PRT
<213> ORGANISM: Artificial Sequence
<220> FEATURE:
<223> OTHER INFORMATION: heavy chain framework region 1 of the humanized
      antibody HuCC49V10

<400> SEQUENCE: 5

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr
            20                  25                  30

<210> SEQ ID NO 6
<211> LENGTH: 14
<212> TYPE: PRT
<213> ORGANISM: Artificial Sequence
<220> FEATURE:
<223> OTHER INFORMATION: heavy chain framework region 2 of the humanized
      antibody HuCC49V10

<400> SEQUENCE: 6

Trp Val Lys Gln Asn Pro Gly Gln Arg Leu Glu Trp Ile Gly
1               5                   10

<210> SEQ ID NO 7
<211> LENGTH: 32
<212> TYPE: PRT
<213> ORGANISM: Artificial Sequence
<220> FEATURE:
<223> OTHER INFORMATION: heavy chain framework region 3 of the humanized
      antibody HuCC49V10

<400> SEQUENCE: 7

Lys Ala Thr Leu Thr Ala Asp Thr Ser Ala Ser Thr Ala Tyr Val Glu
1               5                   10                  15

Leu Ser Ser Leu Arg Ser Glu Asp Thr Ala Val Tyr Phe Cys Thr Arg
            20                  25                  30

<210> SEQ ID NO 8
<211> LENGTH: 11
<212> TYPE: PRT
<213> ORGANISM: Homo sapiens

<400> SEQUENCE: 8

Trp Gly Gln Gly Thr Leu Val Thr Val Ser Ser
1               5                   10

<210> SEQ ID NO 9
<211> LENGTH: 17
<212> TYPE: PRT
<213> ORGANISM: Homo sapiens
```

-continued

```
<400> SEQUENCE: 9

Lys Ser Ser Gln Ser Val Leu Tyr Ser Ser Asn Ser Lys Asn Tyr Leu
1               5                   10                  15

Ala

<210> SEQ ID NO 10
<211> LENGTH: 7
<212> TYPE: PRT
<213> ORGANISM: Homo sapiens

<400> SEQUENCE: 10

Trp Ala Ser Thr Arg Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: light chain CDR3 of the humanized antibody
      HuCC49V10

<400> SEQUENCE: 11

Gln Gln Tyr Tyr Ser Tyr Pro Leu Ser
1               5

<210> SEQ ID NO 12
<211> LENGTH: 5
<212> TYPE: PRT
<213> ORGANISM: Mus musculus

<400> SEQUENCE: 12

Asp His Ala Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: heavy chain CDR2 of the humanized antibody
      HuCC49V10

<400> SEQUENCE: 13

Tyr Phe Ser Pro Gly Asn Asp Asp Phe Lys Tyr Ser Gln Lys Phe Gln
1               5                   10                  15

Gly

<210> SEQ ID NO 14
<211> LENGTH: 6
<212> TYPE: PRT
<213> ORGANISM: Mus musculus

<400> SEQUENCE: 14

Ser Leu Asn Met Ala Tyr
1               5

<210> SEQ ID NO 15
<211> LENGTH: 17
<212> TYPE: PRT
<213> ORGANISM: Homo sapiens

<400> SEQUENCE: 15

Lys Ser Ser Gln Ser Val Leu Tyr Ser Ser Asn Ser Lys Asn Tyr Leu
1               5                   10                  15
```

Ala

<210> SEQ ID NO 16
<211> LENGTH: 7
<212> TYPE: PRT
<213> ORGANISM: Homo sapiens

<400> SEQUENCE: 16

Trp Ala Ser Thr Arg Glu Ser
1               5

<210> SEQ ID NO 17
<211> LENGTH: 9
<212> TYPE: PRT
<213> ORGANISM: Homo sapiens

<400> SEQUENCE: 17

Gln Gln Tyr Tyr Ser Thr Pro Tyr Ser
1               5

<210> SEQ ID NO 18
<211> LENGTH: 5
<212> TYPE: PRT
<213> ORGANISM: Homo sapiens

<400> SEQUENCE: 18

Ser Tyr Ala Met His
1               5

<210> SEQ ID NO 19
<211> LENGTH: 17
<212> TYPE: PRT
<213> ORGANISM: Homo sapiens

<400> SEQUENCE: 19

Trp Ile Asn Ala Gly Asn Gly Asn Thr Lys Tyr Ser Gln Lys Phe Gln
1               5                   10                  15

Gly

<210> SEQ ID NO 20
<211> LENGTH: 10
<212> TYPE: PRT
<213> ORGANISM: Homo sapiens

<400> SEQUENCE: 20

Gly Gly Tyr Tyr Gly Ser Gly Ser Asn Tyr
1               5                   10

<210> SEQ ID NO 21
<211> LENGTH: 23
<212> TYPE: PRT
<213> ORGANISM: Homo sapiens

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 22
<211> LENGTH: 14
<212> TYPE: PRT

```
<400> SEQUENCE: 22

Trp Tyr Gln Gln Lys Pro Gly Gln Pro Pro Leu Leu Ile Tyr
1               5                  10

<210> SEQ ID NO 23
<211> LENGTH: 32
<212> TYPE: PRT
<213> ORGANISM: Homo sapiens

<400> SEQUENCE: 23

Gly Val Pro Asp Arg Phe Ser Gly Ser Gly Ser Gly Thr Asp Phe Thr
1               5                  10                  15

Leu Thr Ile Ser Ser Leu Gln Ala Glu Asp Val Ala Val Tyr Tyr Cys
            20                  25                  30

<210> SEQ ID NO 24
<211> LENGTH: 11
<212> TYPE: PRT
<213> ORGANISM: Homo sapiens

<400> SEQUENCE: 24

Phe Gly Gln Gly Gln Thr Lys Leu Glu Ile Lys
1               5                  10

<210> SEQ ID NO 25
<211> LENGTH: 113
<212> TYPE: PRT
<213> ORGANISM: Artificial Sequence
<220> FEATURE:
<223> OTHER INFORMATION: light chain of humanized antibody HuCC49

<400> SEQUENCE: 25

Asp Ile Val Met Ser Gln Ser Pro Asp Ser Leu Ala Val Ser Leu Gly
1               5                  10                  15

Glu Arg Val Thr Leu Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 26
<211> LENGTH: 30
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr
            20                  25                  30

<210> SEQ ID NO 27
<211> LENGTH: 14
```

-continued

```
<212> TYPE: PRT
<213> ORGANISM: Homo sapiens

<400> SEQUENCE: 27

Trp Val Arg Gln Ala Pro Gly Gln Arg Leu Glu Trp Met Gly
1               5                   10

<210> SEQ ID NO 28
<211> LENGTH: 32
<212> TYPE: PRT
<213> ORGANISM: Homo sapiens

<400> SEQUENCE: 28

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 29
<211> LENGTH: 11
<212> TYPE: PRT
<213> ORGANISM: Homo sapiens

<400> SEQUENCE: 29

Trp Gly Gln Gly Thr Leu Val Thr Val Ser Ser
1               5                   10

<210> SEQ ID NO 30
<211> LENGTH: 115
<212> TYPE: PRT
<213> ORGANISM: Artificial Sequence
<220> FEATURE:
<223> OTHER INFORMATION: heavy chain of humanized antibody HuCC49

<400> SEQUENCE: 30

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
        115

<210> SEQ ID NO 31
<211> LENGTH: 17
<212> TYPE: PRT
<213> ORGANISM: Mus musculus

<400> SEQUENCE: 31

Lys Ser Ser Gln Ser Leu Leu Tyr Ser Gly Asn Gln Lys Asn Tyr Leu
1               5                   10                  15

Ala
```

```
<210> SEQ ID NO 32
<211> LENGTH: 7
<212> TYPE: PRT
<213> ORGANISM: Mus musculus

<400> SEQUENCE: 32

Trp Ala Ser Ala Arg Glu Ser
1               5

<210> SEQ ID NO 33
<211> LENGTH: 9
<212> TYPE: PRT
<213> ORGANISM: Mus musculus

<400> SEQUENCE: 33

Gln Gln Tyr Tyr Ser Tyr Pro Leu Thr
1               5

<210> SEQ ID NO 34
<211> LENGTH: 5
<212> TYPE: PRT
<213> ORGANISM: Mus musculus

<400> SEQUENCE: 34

Asp His Ala Ile His
1               5

<210> SEQ ID NO 35
<211> LENGTH: 17
<212> TYPE: PRT
<213> ORGANISM: Mus musculus

<400> SEQUENCE: 35

Tyr Phe Ser Pro Gly Asn Asp Asp Phe Lys Tyr Asn Glu Arg Phe Lys
1               5                   10                  15

Gly

<210> SEQ ID NO 36
<211> LENGTH: 6
<212> TYPE: PRT
<213> ORGANISM: Mus musculus

<400> SEQUENCE: 36

Ser Leu Asn Met Ala Tyr
1               5

<210> SEQ ID NO 37
<211> LENGTH: 23
<212> TYPE: PRT
<213> ORGANISM: Artificial Sequence
<220> FEATURE:
<223> OTHER INFORMATION: light chain framework region 1 of humanized
      CC49 antibody V35

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 38
<211> LENGTH: 15
<212> TYPE: PRT
<213> ORGANISM: Artificial Sequence
<220> FEATURE:
```

<223> OTHER INFORMATION: light chain framework region 2 of humanized
      CC49 antibody V35

<400> SEQUENCE: 38

Trp Tyr Gln Gln Lys Pro Gly Gln Ser Pro Lys Leu Leu Ile Tyr
1               5                   10                  15

<210> SEQ ID NO 39
<211> LENGTH: 32
<212> TYPE: PRT
<213> ORGANISM: Artificial Sequence
<220> FEATURE:
<223> OTHER INFORMATION: light chain framework region 3 of humanized
      CC49 antibody V35

<400> SEQUENCE: 39

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 40
<211> LENGTH: 10
<212> TYPE: PRT
<213> ORGANISM: Artificial Sequence
<220> FEATURE:
<223> OTHER INFORMATION: light chain framework region 4 of humanized
      CC49 antibody V35

<400> SEQUENCE: 40

Phe Gly Ala Gly Thr Lys Leu Glu Ile Lys
1               5                   10

<210> SEQ ID NO 41
<211> LENGTH: 23
<212> TYPE: PRT
<213> ORGANISM: Artificial Sequence
<220> FEATURE:
<223> OTHER INFORMATION: light chain framework region 1 of humanized
      CC49 antibody V37

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 42
<211> LENGTH: 15
<212> TYPE: PRT
<213> ORGANISM: Artificial Sequence
<220> FEATURE:
<223> OTHER INFORMATION: light chain framework region 2 of humanized
      CC49 antibody V37

<400> SEQUENCE: 42

Trp Tyr Gln Gln Lys Pro Gly Gln Pro Pro Lys Leu Leu Ile Tyr
1               5                   10                  15

<210> SEQ ID NO 43
<211> LENGTH: 32
<212> TYPE: PRT
<213> ORGANISM: Artificial Sequence
<220> FEATURE:
<223> OTHER INFORMATION: light chain framework region 3 of humanized
      CC49 antibody V37

<400> SEQUENCE: 43

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 44
<211> LENGTH: 10
<212> TYPE: PRT
<213> ORGANISM: Artificial Sequence
<220> FEATURE:
<223> OTHER INFORMATION: light chain framework region 4 of humanized
      CC49 antibody V37

<400> SEQUENCE: 44

Phe Gly Gln Gly Thr Lys Leu Glu Ile Lys
1               5                   10

<210> SEQ ID NO 45
<211> LENGTH: 30
<212> TYPE: PRT
<213> ORGANISM: Artificial Sequence
<220> FEATURE:
<223> OTHER INFORMATION: heavy chain framework region 1 of humanized
      CC49 antibody V40

<400> SEQUENCE: 45

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr
            20                  25                  30

<210> SEQ ID NO 46
<211> LENGTH: 14
<212> TYPE: PRT
<213> ORGANISM: Artificial Sequence
<220> FEATURE:
<223> OTHER INFORMATION: heavy chain framework region 2 of humanized
      CC49 antibody V40

<400> SEQUENCE: 46

Trp Val Arg Gln Asn Pro Gly Gln Arg Leu Glu Trp Met Gly
1               5                   10

<210> SEQ ID NO 47
<211> LENGTH: 32
<212> TYPE: PRT
<213> ORGANISM: Artificial Sequence
<220> FEATURE:
<223> OTHER INFORMATION: heavy chain framework region 3 of humanized
      CC49 antibody V40

<400> SEQUENCE: 47

Arg Val Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
            20                  25                  30

<210> SEQ ID NO 48
<211> LENGTH: 11
<212> TYPE: PRT
<213> ORGANISM: Homo sapiens

<400> SEQUENCE: 48

Trp Gly Gln Gly Thr Leu Val Thr Val Ser Ser
1               5                   10

<210> SEQ ID NO 49
<211> LENGTH: 30
<212> TYPE: PRT
<213> ORGANISM: Artificial Sequence
<220> FEATURE:
<223> OTHER INFORMATION: heavy chain framework region 1 of humanized
      CC49 antibody V41

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 50
<211> LENGTH: 14
<212> TYPE: PRT
<213> ORGANISM: Artificial Sequence
<220> FEATURE:
<223> OTHER INFORMATION: heavy chain framework region 2 of humanized
      CC49 antibody V41

<400> SEQUENCE: 50

Trp Val Arg Gln Ala Pro Gly Gln Arg Leu Glu Trp Met Gly
1               5                   10

<210> SEQ ID NO 51
<211> LENGTH: 32
<212> TYPE: PRT
<213> ORGANISM: Artificial Sequence
<220> FEATURE:
<223> OTHER INFORMATION: heavy chain framework region 3 of humanized
      CC49 antibody V41

<400> SEQUENCE: 51

Arg Val Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
            20                  25                  30

<210> SEQ ID NO 52
<211> LENGTH: 11
<212> TYPE: PRT
<213> ORGANISM: Homo sapiens

<400> SEQUENCE: 52

Trp Gly Gln Gly Thr Leu Val Thr Val Ser Ser
1               5                   10

<210> SEQ ID NO 53
<211> LENGTH: 25
<212> TYPE: DNA
<213> ORGANISM: Artificial Sequence
<220> FEATURE:
<223> OTHER INFORMATION: Oligonucleotide primer/probe

<400> SEQUENCE: 53
gtctggagac tgggtcatca cgatg                                           25

<210> SEQ ID NO 54
<211> LENGTH: 30
<212> TYPE: DNA
<213> ORGANISM: Artificial Sequence
<220> FEATURE:
<223> OTHER INFORMATION: Oligonucleotide primer/probe

<400> SEQUENCE: 54

```
ggacttgcaa ttgatagtgg ccctctcgcc                                     30

<210> SEQ ID NO 55
<211> LENGTH: 24
<212> TYPE: DNA
<213> ORGANISM: Artificial Sequence
<220> FEATURE:
<223> OTHER INFORMATION: Oligonucleotide primer/probe

<400> SEQUENCE: 55
ccagggcagc tcctaaact gctg                                            24

<210> SEQ ID NO 56
<211> LENGTH: 24
<212> TYPE: DNA
<213> ORGANISM: Artificial Sequence
<220> FEATURE:
<223> OTHER INFORMATION: Oligonucleotide primer/probe

<400> SEQUENCE: 56
cagcagttta ggaggctgcc ctgg                                           24

<210> SEQ ID NO 57
<211> LENGTH: 24
<212> TYPE: DNA
<213> ORGANISM: Artificial Sequence
<220> FEATURE:
<223> OTHER INFORMATION: Oligonucleotide primer/probe

<400> SEQUENCE: 57
caatcagcag cctgcaggca gaag                                           24

<210> SEQ ID NO 58
<211> LENGTH: 35
<212> TYPE: DNA
<213> ORGANISM: Artificial Sequence
<220> FEATURE:
<223> OTHER INFORMATION: Oligonucleotide primer/probe

<400> SEQUENCE: 58
gcagccgcgg cccgtttgat ttccagcttg gtgcc                               35

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide primer/probe

<400> SEQUENCE: 59
cagcttggtg ccctggccga agctgagg                                       28

<210> SEQ ID NO 60
<211> LENGTH: 41
<212> TYPE: DNA
<213> ORGANISM: Artificial Sequence
<220> FEATURE:
<223> OTHER INFORMATION: Oligonucleotide primer/probe

<400> SEQUENCE: 60
gcagccgcgg cccgtttgat ttccagcttg gtgccctggc c                        41

<210> SEQ ID NO 61
<211> LENGTH: 24
<212> TYPE: DNA
<213> ORGANISM: Artificial Sequence
```

```
<220> FEATURE:
<223> OTHER INFORMATION: Oligonucleotide primer/probe

<400> SEQUENCE: 61
ccccaggttt cttcacctca gcgc                                          24

<210> SEQ ID NO 62
<211> LENGTH: 25
<212> TYPE: DNA
<213> ORGANISM: Artificial Sequence
<220> FEATURE:
<223> OTHER INFORMATION: Oligonucleotide primer/probe

<400> SEQUENCE: 62
ccttgcagga caccttcacg gaagc                                         25

<210> SEQ ID NO 63
<211> LENGTH: 54
<212> TYPE: DNA
<213> ORGANISM: Artificial Sequence
<220> FEATURE:
<223> OTHER INFORMATION: Oligonucleotide primer/probe

<400> SEQUENCE: 63
ccactgggtg agacagaatc ctggacagcg cctggagtgg atgggatatt tctc         54

<210> SEQ ID NO 64
<211> LENGTH: 54
<212> TYPE: DNA
<213> ORGANISM: Artificial Sequence
<220> FEATURE:
<223> OTHER INFORMATION: Oligonucleotide primer/probe

<400> SEQUENCE: 64
gagaaatatc ccatccactc caggcgctgt ccaggattct gtctcaccca gtgg         54

<210> SEQ ID NO 65
<211> LENGTH: 23
<212> TYPE: DNA
<213> ORGANISM: Artificial Sequence
<220> FEATURE:
<223> OTHER INFORMATION: Oligonucleotide primer/probe

<400> SEQUENCE: 65
ggtgagacag gctcctggac agc                                           23

<210> SEQ ID NO 66
<211> LENGTH: 33
<212> TYPE: DNA
<213> ORGANISM: Artificial Sequence
<220> FEATURE:
<223> OTHER INFORMATION: Oligonucleotide primer/probe

<400> SEQUENCE: 66
gttccagggc agggtgacca tcactgcaga cac                                33

<210> SEQ ID NO 67
<211> LENGTH: 33
<212> TYPE: DNA
<213> ORGANISM: Artificial Sequence
<220> FEATURE:
<223> OTHER INFORMATION: Oligonucleotide primer/probe

<400> SEQUENCE: 67
gtgtctgcag tgatggtcac cctgccctgg aac                                33
```

```
<210> SEQ ID NO 68
<211> LENGTH: 26
<212> TYPE: DNA
<213> ORGANISM: Artificial Sequence
<220> FEATURE:
<223> OTHER INFORMATION: Oligonucleotide primer/probe

<400> SEQUENCE: 68
gcactgccta catggagctc tccagc                                          26

<210> SEQ ID NO 69
<211> LENGTH: 30
<212> TYPE: DNA
<213> ORGANISM: Artificial Sequence
<220> FEATURE:
<223> OTHER INFORMATION: Oligonucleotide primer/probe

<400> SEQUENCE: 69
gtgtacttct gcgccagatc cctgaatatg                                      30

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide primer/probe

<400> SEQUENCE: 70
gcaagcttcc accatggata                                                 20

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide primer/probe

<400> SEQUENCE: 71
ctagaattcc accatggagt ggtcc                                           25

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide primer/probe

<400> SEQUENCE: 72
atgggcccgt agttttggcg c                                               21

<210> SEQ ID NO 73
<211> LENGTH: 23
<212> TYPE: PRT
<213> ORGANISM: Mus musculus

<400> SEQUENCE: 73

Asp Ile Val Met Ser Gln Ser Pro Ser Ser Leu Pro Val Ser Val Gly
 1               5                  10                  15

Glu Lys Val Thr Leu Ser Cys
            20

<210> SEQ ID NO 74
<211> LENGTH: 15
<212> TYPE: PRT
<213> ORGANISM: Mus musculus

<400> SEQUENCE: 74
```

```
Trp Tyr Gln Gln Lys Pro Gly Gln Ser Pro Lys Leu Leu Ile Tyr
1               5                   10                  15
```

<210> SEQ ID NO 75
<211> LENGTH: 32
<212> TYPE: PRT
<213> ORGANISM: Mus musculus

<400> SEQUENCE: 75

```
Gly Val Pro Asp Arg Phe Thr Gly Ser Gly Ser Gly Thr Asp Phe Thr
1               5                   10                  15

Leu Ser Ile Ser Ser Val Lys Thr Glu Asp Leu Ala Val Tyr Tyr Cys
            20                  25                  30
```

<210> SEQ ID NO 76
<211> LENGTH: 10
<212> TYPE: PRT
<213> ORGANISM: Mus musculus

<400> SEQUENCE: 76

```
Phe Gly Ala Gly Thr Lys Leu Val Leu Lys
1               5                   10
```

<210> SEQ ID NO 77
<211> LENGTH: 30
<212> TYPE: PRT
<213> ORGANISM: Mus musculus

<400> SEQUENCE: 77

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr
            20                  25                  30
```

<210> SEQ ID NO 78
<211> LENGTH: 14
<212> TYPE: PRT
<213> ORGANISM: Mus musculus

<400> SEQUENCE: 78

```
Trp Val Lys Gln Asn Pro Glu Gln Gly Leu Glu Trp Ile Gly
1               5                   10
```

<210> SEQ ID NO 79
<211> LENGTH: 32
<212> TYPE: PRT
<213> ORGANISM: Mus musculus

<400> SEQUENCE: 79

```
Lys Ala Thr Leu Thr Ala Asp Lys Ser Ser Ser Thr Ala Tyr Val Gln
1               5                   10                  15

Leu Asn Ser Leu Thr Ser Glu Asp Ser Ala Val Tyr Phe Cys Thr Arg
            20                  25                  30
```

<210> SEQ ID NO 80
<211> LENGTH: 11
<212> TYPE: PRT
<213> ORGANISM: Mus musculus

<400> SEQUENCE: 80

```
Trp Gly Gln Gly Thr Ser Val Thr Val Ser Ser
1               5                   10
```

```
<210> SEQ ID NO 81
<211> LENGTH: 113
<212> TYPE: PRT
<213> ORGANISM: Mus musculus

<400> SEQUENCE: 81

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 82
<211> LENGTH: 115
<212> TYPE: PRT
<213> ORGANISM: Mus musculus

<400> SEQUENCE: 82

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115
```

NUCLEIC ACID MOLECULES ENCODING MINIMALLY IMMUNOGENIC VARIANTS OF SDR-GRAFTED HUMANIZED ANTIBODY CC49

PRIORITY CLAIM

This is a divisional of U.S. patent application Ser. No. 10/570,220, filed Feb. 28, 2006, now issued as U.S. Pat. No. 7,589,181, which is the §371 U.S. National Stage of International Application No. PCT/US2004/028004, filed Aug. 27, 2004, which was published in English under PCT Article 21(2), which in turn claims the benefit of U.S. Provisional Application No. 60/498,903, filed Aug. 29, 2003, the contents of all of which are hereby incorporated by reference.

FIELD

The present disclosure relates to humanized monoclonal antibodies that bind a tumor antigen. More specifically, the present disclosure relates to humanized monoclonal antibodies with non-conservative amino acid substitutions that have a high binding affinity for tumor-associated glycoprotein (TAG)-72 and minimal immunogenicity.

BACKGROUND

The use of murine monoclonal antibodies in medicine has significant potential especially in the diagnosis and treatment of various diseases, including cancer. The advantage of using monoclonal antibodies resides is their specificity for a single antigen. A monoclonal antibody raised against a specific tumor cell surface antigen can be coupled to therapeutic agents, such as radioisotopes and chemotherapeutic drugs, and these immunoconjugates can be used clinically to specifically target, for example, a tumor cell of interest.

A major limitation in the clinical use of monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). A more recent method in the humanization procedure is based on grafting, onto the variable (VL) and variable heavy (VH) frameworks of human monoclonal antibodies (mAb), of the specificity determining residues (SDRs), the CDR residues that are crucial for the complementarity of the antigen (Ag):Ab surfaces (Kashmiri et al., *Crit. Rev. Oncol. Hematol.* 38: 3-16, 2001). In generating humanized Abs, whether by grafting CDRs or SDRs, a few murine framework residues considered crucial for the maintenance of the Ab combining sites are also transplanted onto the human frameworks (for example, see Abola et al., *Methods Enzymol* 277, 556-71, 1997).

Murine CC49 (mCC49) is an antibody that specifically recognizes a tumor-associated glycoprotein (TAG)-72 expressed on a majority of human carcinomas (Muraro et al., *Cancer Res.* 48:4588-4596, 1988). These antibodies have been shown to efficiently target colorectal (Divgi et al., *J Nucl Med* 36:586-592, 1995; Divgi et al., *Clin Cancer Res* 1:1503-1510, 1995; Liu et al., *Cancer Biother Radiopharm* 12:79-87, 1997; Meredith et al., *Clin Cancer Res* 2:1811-1818, 1996; Rucker et al., *J Immunother* 22:80-84, 1999; Tempero et al., *J Clin Oncol* 15:1518-1528, 1997), breast (Macey et al., *Clin Cancer Res* 3:1547-1555, 1997; Murray et al., *Cancer Res* 55:5925s-5928s, 1995), ovarian (Alvarez et al., *Gynecol Oncol* 65:94-101, 1997; Meredith et al., *Cancer Biother Radiopharm* 16:305-315, 2001; Meredith et al., *J Nucl Med* 37:1491-1496, 1996), and prostate (Liu et al., *Cancer Biother Radiopharm* 12-7987, 1997; Meredith et al., *Clin Cancer Res* 5:3254s-3258s, 1999; Slovin et al., *Clin Cancer Res* 4:643-651, 1998) carcinomas in several phase I/II clinical trials. As a therapeutic reagent, humanized CC49 ($^{177}$Lu-mCC49) has been found to evoke objective responses in ovarian cancer patients (Alvarez et al., *Gynecol Oncol* 65:94-101, 1997; Meredith et al., *Cancer Biother Radiopharm* 16:305-315, 2001; Meredith et al., *J Nucl Med* 37:1491-1496, 1996), while objective responses have also been reported in metastatic breast and prostate cancer patients administered with one or two doses of $^{131}$I-mCC49 (Macey et al., *Clin Cancer Res* 3:1547-1555, 1997; Meredith et al., *Clin Cancer Res* 5:3254s-3258s, 1999). mCC49 has also been used in radioimmunoguided surgery, which is more sensitive in detecting metastases than the traditional clinical and histological examinations (Cote et al., *Cancer* 77:613-620, 1996; LaValle et al., *Surgery* 122:867-871, 1997; McIntosh et al., *Cancer Biother Radiopharm* 12:287-294, 1997), thus resulting in better disease staging (Haddad et al., *Eur J Surg Oncol* 27:298-301, 2001; Schneebaum et al., *Recent Results Cancer Res* 157:281-292, 2000).

Unfortunately, the clinical utility of the mCC49 monoclonal antibody has been limited because of its murine origin. Thus, there clearly exists a need to develop a humanized CC49 antibody with both high antigen binding affinity and low immunogenicity for use in human subjects.

SUMMARY

Humanized anti-TAG-72 CC49 monoclonal antibodies are disclosed herein. The antibodies are variants of a humanized CC49 antibody that are specifically designed to minimize immunogenicity in human subjects. The antibodies are also designed to retain or improve the binding specificity for TAG-72. In one example, the antibodies are produced by genetic manipulation of the framework region of HuCC49V10.

In one embodiment, the antibodies include a light chain Complementarity Determining Region (L-CDR)1, an L-CDR2, and an L-CDR3; and a heavy chain Complementarity Determining Region (H-CDR)1, an H-CDR2, and an H-CDR3 from humanized antibody HuCC49V10. The L-CDR1, L-CDR2, L-CDR3 are within a HuCC49V10 light chain framework region that includes the corresponding amino acid from LEN at position 5, 19, 21, and 106 in the light chain. The H-CDR1, H-CDR2, and H-CDR3 are within a heavy chain HuCC49V10 framework comprising a human 21/28' CL residue at positions 20, 38, 48, 66, 67, 69, and 80 in the heavy chain. These humanized CC49 antibodies retain binding affinity for TAG-72 and have reduced immunogenicity, as compared to a parental Hu-CC49 V10 antibody.

In another embodiment, the antibodies include an L-CDR1 from HuCC49V14, and an L-CDR2, an L-CDR3, an H-CDR-1, an H-CDR2, and an H-CDR3 from humanized antibody HuCC49V10. The L-CDR1, L-CDR2, L-CDR3 are within a HuCC49V10 light chain framework region that includes the corresponding amino acid from LEN at position 5, 19, 21, and 106 in the light chain. The H-CDR1, H-CDR2, and H-CDR3 are within a heavy chain HuCC49V10 framework comprising a human 21/28' CL residue at positions 20, 38, 48, 66, 67, 69, and 80 in the heavy chain. These humanized CC49 antibodies retain binding affinity for TAG-72 and have reduced immunogenicity, as compared to a parental HuCC49V10 antibody.

In a further embodiment, the antibodies include an L-CDR1 and an L-CDR3 from HuCC49V15, an L-CDR2, an H-CDR1, an H-CDR2, and an H-CDR3 from humanized antibody HuCC49V10. The L-CDR1, L-CDR2, L-CDR3 are within a HuCC49V10 light chain framework region that includes the corresponding amino acid from LEN at position 5, 19, 21, and 106 in the light chain. The H-CDR1, H-CDR2, and H-CDR3 are within a heavy chain HuCC49V10 framework comprising a human 21/28' CL residue at positions 20, 38, 48, 66, 67, 69, and 80 in the heavy chain. These humanized CC49 antibodies retain binding affinity for TAG-72 and have reduced immunogenicity, as compared to a parental HuCC49V10 antibody.

Methods are disclosed herein for using these antibodies for treating a tumor expressing TAG-72. Methods are also disclosed herein for using these antibodies to detect tumor cells expressing TAG-72.

The foregoing and other features and advantages will become more apparent from the following detailed description of several embodiments, which proceeds with reference to the accompanying figures.

BRIEF DESCRIPTION OF THE FIGURES

FIG. 8 is a digital image showing a comparison of the CDR sequences of murine MAb CC49 and humanized MAb HuCC49 with the corresponding CDR sequences of human MAbs LEN and 21/28'CL. Amino acid residues are numbered using the convention of Kabat et al. (*Sequences of Proteins of Immunological Interest*, 5th Edition, Department of Health and Human Services, Public Health Service, National Institutes of Health, Bethesda (NIH Publication No. 91-3242), 1991) The underlined numbers indicate the specificity determining residues (SDRs). CDR1, CDR2 and CDR3 within the light chain of HuCC49 and CC49 correspond to SEQ ID NOs: 31-33, respectively (SEQ ID NOs: 1-3 of U.S. application Ser. No. 09/830,748, which is incorporated herein by reference). CDR1, CDR2 and CDR3 within the heavy chain of HuCC49 and CC49 correspond to SEQ ID NOs: 34-36, respectively (SEQ ID NOs: 4-6 of US. application Ser. No. 09/830,748 (now U.S. Pat. No. 6,818,749), which is incorporated herein by reference). CDR1, CDR2 and CDR3 within the light chain of human antibody LEN correspond to SEQ ID NOs: 15-17, respectively. CDR1, CDR2 and CDR3 within the heavy chain of human antibody 21/28'CL correspond to SEQ ID NOs: 18-20, respectively (SEQ ID NOs: 10-12 of U.S. application Ser. No. 09/830,748 (now U.S. Pat. No. 6,818,749), which is incorporated herein by reference). In HuCC49V10, amino acid 60 is a serine, amino acid 61 is a glutamine, amino acid 62 is a lysine, amino acid 64 is a glutamine in the heavy chain, and amino acid 97 is a threonine in the light chain.

FIG. 9A shows the amino acid sequence of the VL frameworks of human MAb LEN (SEQ ID NOs: 21-24) (see also U.S. application Ser. No. 09/830,748 (now U.S. Pat. No. 6,818,749), which is incorporated herein by reference), the entire sequence of the VL region of humanized CC49 (HuCC49, SEQ ID NO: 25) including the frameworks and CDRs, and the entire sequence of the VL region of the murine CC49 (mCC49, SEQ ID NO: 81), including frameworks and CDRs. FIG. 9B shows the amino acid sequences of VH frameworks of human mAb 21/28'CL (SEQ ID NOs: 26-29), the entire sequence of the VH region of HuCC49, including the frameworks and CDRs (SEQ ID NO: 30), and the entire sequence of the VH region of the murine CC49 (SEQ ID NOs: 82). The sequence of the mCC49 CDRs are individually set forth as SEQ NOs: 31-36. Framework residues previously deemed to be important in maintaining the combining site structure of CC49 on the basis of structure are marked by an asterisk. Those murine framework residues deemed important for binding, and that are different from the residue at the corresponding position in the human sequences, were retained (see also U.S. application Ser. No. 09/830,748 (now U.S. Pat. No. 6,818,749), which is incorporated herein by reference).

SEQUENCE LISTING

Figure 1:
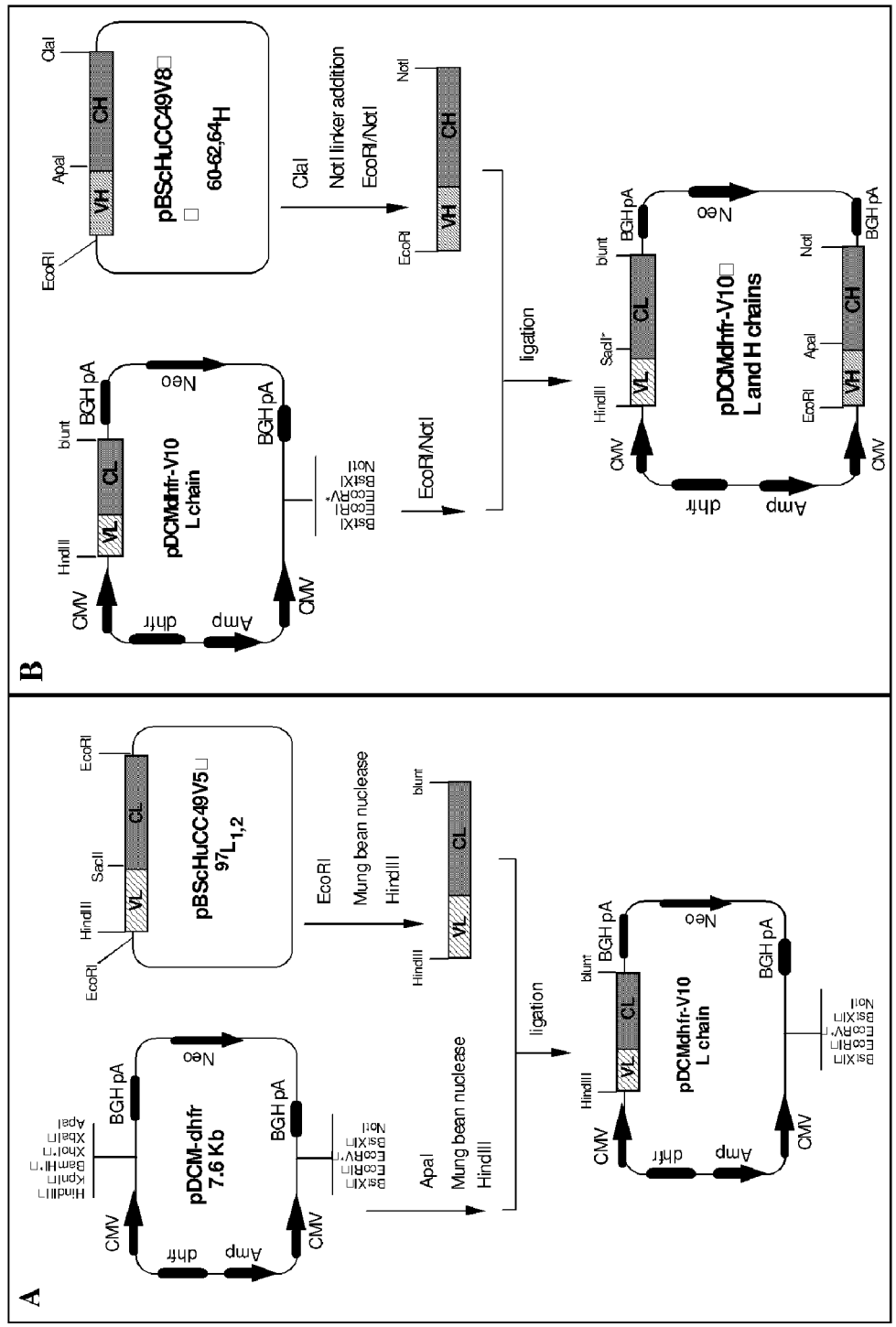
FIGS. 1A-B are schematic diagrams of the generation of the expression constructs derived from the genes encoding the light (L) and heavy (H) chains of the framework variants of HuCC49V10. The pDCM-dhfr vector was used to generate the expression construct of the L chain (pDCMdhfrV10 L chain), as shown in FIG. 1A. Expression constructs of the framework variants containing mutations in the L chain were generated by swapping the appropriate PCR-amplified $V_L$ region sequences with the $V_L$ sequence of HuCC49V10 in this DNA construct through the HindIII/SacII site, prior to insertion of the appropriate H chain sequence into the vector. Generation of the dual expression construct of the L and H chains of HuCC49V10 (pDCMdhfrV10 L and H chains) is shown in FIG. 1B. To generate constructs containing the genes of the H chain framework variants, the suitable PCR-amplified $V_H$ sequences were exchanged with the HuCC49V10 $V_H$ sequence through the unique EcoRI/ApaI site in the pDCMdhfr construct containing the L and H chains of HuCC49V10. CMV, human cytomegalovirus promoter; BGH pA, bovine growth hormone polyadenylation signal sequence; Amp, ampicillin[r]; dhfr, dihydrofolate reductase gene; Neo, neomycin[r] gene; $C_L$ and $C_H$, constant regions of human κ and γ1 chains.

The amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of FR1 of the light chain of HuCC49V10.

SEQ ID NO: 2 is the amino acid sequence of FR2 of the light chain of HuCC49V10.

SEQ ID NO: 3 is the amino acid sequence of FR3 of the light chain of HuCC49V10.

SEQ ID NO: 4 is the amino acid sequence of FR4 of the light chain of HuCC49V10.

SEQ ID NO: 5 is the amino acid sequence of FR1 of the heavy chain of HuCC49V10.

SEQ ID NO: 6 is the amino acid sequence of FR2 of the heavy chain of HuCC49V10.

SEQ ID NO: 7 is the amino acid sequence of FR3 of the heavy chain of HuCC49V10.

SEQ ID NO: 8 is the amino acid sequence of FR4 of the heavy chain of HuCC49V10.

SEQ ID NO: 9 is the amino acid sequence of the LCDR1 of HuCC49V10.

SEQ ID NO: 10 is the amino acid sequence of the LCDR2 of HuCC49V10.

SEQ ID NO: 11 is the amino acid sequence of the LCDR3 of HuCC49V10.

SEQ ID NO: 12 is the amino acid sequence of the HCDR1 of HuCC49V10.

SEQ ID NO: 13 is the amino acid sequence of the HCDR2 of HuCC49V10.

SEQ ID NO: 14 is the amino acid sequence of the HCDR3 of HuCC49V10.

SEQ ID NO: 15 is the amino acid sequence of the LCDR1 of LEN.

SEQ ID NO: 16 is the amino acid sequence of the LCDR2 of LEN.

SEQ ID NO: 17 is the amino acid sequence of the LCDR3 of LEN.

SEQ ID NO: 18 is the amino acid sequence of the HCDR1 of 21/28'CL.

SEQ ID NO: 19 is the amino acid sequence of the HCDR2 of 21/28'CL.

SEQ ID NO: 20 is the amino acid sequence of the HCDR3 of 21/28'CL.

SEQ ID NO: 21 is the amino acid sequence of the light chain FR1 of LEN.

SEQ ID NO: 22 is the amino acid sequence of the light chain FR2 of LEN.

SEQ ID NO: 23 is the amino acid sequence of the light chain FR3 of LEN.

SEQ ID NO: 24 is the amino acid sequence of the light chain FR4 of LEN.

SEQ ID NO: 25 is the amino acid sequence of the variable light chain of HuCC49.

SEQ ID NO: 26 is the amino acid sequence of the light chain FR1 of 21/28'CL.

SEQ ID NO: 27 is the amino acid sequence of the light chain FR2 of 21/28'CL.

SEQ ID NO: 28 is the amino acid sequence of the light chain FR3 of 21/28'CL.

SEQ ID NO: 29 is the amino acid sequence of the light chain FR4 of 21/28'CL.

SEQ ID NO: 30 is the amino acid sequence of the variable heavy chain of HuCC49.

SEQ ID NO: 31 is the amino acid sequence of the LCDR1 of CC49 and HuCC49.

SEQ ID NO: 32 is the amino acid sequence of the LCDR2 of CC49 and HuCC49.

SEQ ID NO: 33 is the amino acid sequence of the LCDR3 of CC49 and HuCC49.

SEQ ID NO: 34 is the amino acid sequence of the HCDR1 of CC49 and HuCC49.

SEQ ID NO: 35 is the amino acid sequence of the HCDR2 of CC49 and HuCC49.

SEQ ID NO: 36 is the amino acid sequence of the HCDR3 of CC49 and HuCC49.

SEQ ID NO: 37 is the amino acid sequence of the FR1 of V35.

SEQ ID NO: 38 is the amino acid sequence of the FR2 of V35.

SEQ ID NO: 39 is the amino acid sequence of the FR3 of V35.

SEQ ID NO: 40 is the amino acid sequence of the FR4 of V35.

SEQ ID NO: 41 is the amino acid sequence of the FR1 of V37.

SEQ ID NO: 42 is the amino acid sequence of the FR2 of V37.

SEQ ID NO: 43 is the amino acid sequence of the FR3 of V37.

SEQ ID NO: 44 is the amino acid sequence of the FR4 of V37.

SEQ ID NO: 45 is the amino acid sequence of the FR1 of V40.

SEQ ID NO: 46 is the amino acid sequence of the FR2 of V40.

SEQ ID NO: 47 is the amino acid sequence of the FR3 of V40.

SEQ ID NO: 48 is the amino acid sequence of the FR4 of V40.

SEQ ID NO: 49 is the amino acid sequence of the FR1 of V41.

SEQ ID NO: 50 is the amino acid sequence of the FR2 of V41.

SEQ ID NO: 51 is the amino acid sequence of the FR3 of V41.

SEQ ID NO: 52 is the amino acid sequence of the FR4 of V41.

SEQ ID NOs: 53-72 are the nucleic acid sequence of primers.

SEQ ID NO: 73 is the amino acid sequence of the light chain FR1 of the murine CC49 (mCC49).

SEQ ID NO: 74 is the amino acid sequence of the light chain FR2 of the murine CC49 (mCC49).

SEQ ID NO: 75 is the amino acid sequence of the light chain FR3 of the murine CC49 (mCC49).

SEQ ID NO: 76 is the amino acid sequence of the light chain FR4 of the murine CC49 (mCC49).

SEQ ID NO: 77 is the amino acid sequence of the heavy chain FR1 of the murine CC49 (mCC49).

SEQ ID NO: 78 is the amino acid sequence of the heavy chain FR2 of the murine CC49 (mCC49).

SEQ ID NO: 79 is the amino acid sequence of the heavy chain FR3 of the murine CC49 (mCC49).

SEQ ID NO: 80 is the amino acid sequence of the heavy chain FR4 of the murine CC49 (mCC49).

SEQ ID NO: 81 is the amino acid sequence of the variable light chain of mCC49.

SEQ ID NO: 82 is the amino acid sequence of the variable heavy chain of mCC49.

DETAILED DESCRIPTION

I. Abbreviations
Ab antibody
Ag antigen
BSM bovine submaxillary mucin
C constant
CH constant heavy
CHO Chinese hamster ovary
CL constant light
CDR complementarity determining region
ELISA enzyme-linked immunosorbent assay
Fab fragment antigen binding
$F(ab')_2$ Fab with additional amino acids, including cysteines necessary for disulfide bonds
FACS fluorescence activated cell sort
FR framework region
Fv fragment variable
H heavy
HAMA human antimurine antibody
HuIgG human immunoglobulin G
$IC_{50}$ half maximal inhibition of binding
Ig immunoglobulin
IL interleukin
Ka relative affinity constant
L light
mCC49 murine CC49
m.w. molecular weight
PCR polymerase chain reaction
PDB protein data bank
RIA radioimmunoassay
RU resonance unit
scFv single chain Fv
SDR specificity determining residue
SPR surface plasmon resonance
SSKI saturated solution of potassium iodide
TAG-72 tumor associated glycoprotein-72
TNF tumor necrosis factor
V variable
VH variable heavy
VL variable light
V10 HuCC49V10

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin (Ig) molecules and immunologically active portions of Ig molecules, for instance, molecules that contain an antigen binding site which specifically binds (immunoreacts with) an antigen.

A naturally occurring antibody (for example, IgG) includes four polypeptide chains, two heavy (H) chains and two light (L) chains interconnected by disulfide bonds. The two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE.

Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors. The specificity of the antibody resides in the structural complementarity between the antibody combining site and the antigenic determinant. Antibody combining sites are made up of residues that are primarily from the hypervariable or complementarity determining regions (CDRs). However, it is believed that residues from nonhypervariable or framework regions (FR) influence the overall domain structure and hence the combining site.

It has been shown that the antigen-binding function of an antibody can be performed by fragments of a naturally occurring antibody. Thus, these antigen-binding fragments are also intended to be designated by the term "antibody." Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-546, 1989) which consists of a VH domain; and (v) an $F(ab')_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); (Bird et al., *Science* 242:423-426, 1988; and Huston et al., *Proc. Natl. Acad. Sci.* 85:5879-5883, 1988) by recombinant methods. Such single chain antibodies, as well as dsFv, a disulfide stabilized Fv (Bera et al., *J. Mol. Biol.* 281:475-483, 1998), and dimeric Fvs (diabodies), that are generated by pairing different polypeptide chains (Holliger et al., *Proc. Natl. Acad. Sci.* 90:6444-6448, 1993), are also included.

In one embodiment, antibody fragments for use in this disclosure are those which are capable of cross-linking their target antigen, for example, bivalent fragments such as F(ab')$_2$ fragments. Alternatively, an antibody fragment which does not itself cross-link its target antigen (for example, a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. In one embodiment, the antigen is TAG-72. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody."

In one embodiment the antigen is tumor-associated glycoprotein (TAG-72). Monoclonal, and humanized immunoglobulins are encompassed by the disclosure. In one example, a murine monoclonal antibody that recognizes the TAG-72 antigen is CC49. In another example, a humanized CC49 antibody is HuCC49. In other examples, a humanized CC49 antibody includes a light chain from HuCC49V10 variants V35 or V37, and/or a heavy chain from HuCC49V10 variants V40 or V41. In several examples, variant humanized CC49 antibodies are HuCC49V48 ("V48"), HuCC49V47 ("V47"), HuCC49V58 ("V58") or HuCC49V59 ("V59"). The disclosure also includes synthetic and genetically engineered variants of these immunoglobulins.

Antigen: Any molecule that can bind specifically with an antibody. An antigen is also a substance that evokes immune response, including production of antibodies. Antigens are often foreign substances such as allergens, bacteria or viruses that invade the body. A specific, non-limiting example of an antigen is TAG-72.

CC49 monoclonal antibody: A murine monoclonal antibody of the IgG$_1$ isotype that specifically binds TAG-72 (deposited as ATCC Accession No. HB 9459). This monoclonal antibody is a second generation monoclonal antibody prepared by immunizing mice with TAG-72 that was purified using the first generation antibody B72.3 (Colcher et al., *Proc. Natl. Acad. Sci. USA* 78:3199-3203, 1981). The murine CC49 (mCC49) monoclonal antibody efficiently targets human colon carcinoma xenografts in athymic mice and reduces or eliminates their growth (Colcher et al., *Cancer Res.* 48:4597-4603, 1988). Radiolabeled CC49 has been shown to successfully target a number of human tumors including adenocarcinoma, colorectal, breast, prostate and ovarian (Liu et al., *Cancer Biother Radiopharm.* 12:79-87, 1997; Macey et al., *Clin. Cancer Res.* 3:1547-1555, 1997; Meredith et al., *J. Nucl. Med.,* 37:1491-1496, 1996.)

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chimeric antibody: An antibody which includes sequences derived from two different antibodies, which typically are of different species. Most typically, chimeric antibodies include human and murine antibody domains, generally human constant regions and murine variable regions, murine CDRs and/or murine SDRs.

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest,* 5$^{th}$ Edition, Department of Health and Human Services, Public Health Service, National Institutes of Health, Bethesda (NIH Publication No. 91-3242).

Constant Region: The portion of the antibody molecule which confers effector functions. In the present disclosure, the variant antibodies include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type.

Cytotoxin: An agent that is toxic for cells. Examples of cytotoxins include radioactive isotopes, chemotherapeutic drugs, bacterial toxins, viral toxins, and proteins contained in venom (for example, insect, reptile, or amphibian venom). A cytokine, such as interleukin-2 or interferon, can also be a cytotoxin.

Diagnostically effective amount: A quantity of a specific substance sufficient to achieve a desired effect in a subject or tissue being diagnosed. For instance, this can be the amount necessary to detect the presence of a tumor. In one embodiment, a diagnostically effective amount is the amount necessary to detect a tumor expressing TAG-72. When administered to a subject, a dosage will generally be used that will achieve target tissue concentrations (for example, in tumors) that has been shown to achieve a desired in vitro effect.

DNA: Deoxyribonucleic acid. DNA is a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

Effector Molecule: Therapeutic, diagnostic or detection moieties linked to an antibody, using any number of means known to those of skill in the art. Both covalent and noncovalent linkage means may be used. The procedure for linking an effector molecule to an antibody varies according to the chemical structure of the effector. Polypeptides typically contain a variety of functional groups; for example, carboxylic acid (COOH), free amino (—NH$_2$) or sulfhydryl (—SH) groups, which are available for reaction with a suitable functional group on an antibody to result in the linkage of the effector molecule. Alternatively, the antibody is derivatized to expose or link additional reactive functional groups. The derivatization may involve linkage of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (for example, through a disulfide linkage to cysteine) or to the alpha carbon amino and carboxyl groups of the terminal amino acids.

An "immunoconjugate" is a covalent linkage of an effector molecule, such as a toxin, a chemical compound, or a detectable label, to an antibody. Specific, non-limiting examples of toxins include, but are not limited to, abrin, ricin, *Pseudomonas* exotoxin (such as PE35, PE37, PE38, and PE40), diphtheria toxin, anthrax toxin, botulinum toxin, or modified toxins thereof. For example, *Pseudomonas* exotoxin and diphtheria toxin are highly toxic compounds that typically bring about death through liver toxicity. *Pseudomonas* exotoxin and diphtheria toxin, however, can be modified into a form for use as an immunotoxin by removing the native targeting component of the toxin (for example, domain Ia of *Pseudomonas* exotoxin and the B chain of diphtheria toxin) and replacing it with a different targeting moiety, such as an antibody. Other toxic agents, that directly or indirectly inhibit cell growth or kill cells, include chemotherapeutic drugs, cytokines, for example interleukin (IL)-2, IL-4, IL-10, tumor necrosis factor-alpha, or interferon-gamma, radioactive isotopes, viral toxins, or proteins contained within, for example, insect, reptile, or amphibian venom. Specific, non-limiting examples of detectable labels include, but are not limited to, radioactive isotopes, enzyme substrates, co-factors, ligands, chemiluminescent agents, fluorescent agents, haptens, or enzymes.

In one embodiment, an antibody is joined to an effector molecule. In another embodiment, an antibody joined to an effector molecule is further joined to a lipid or other molecule to a protein or peptide to increase its half-life in the antibody. The linkage can be, for example, either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example, when exposed to tumor-associated enzymes or acidic pH) may be used.

In view of the large number of methods that have been reported for linking a variety of radiodiagnostic compounds, radiotherapeutic compounds, label (for example, enzymes or fluorescent molecules) drugs, toxins, and other agents to antibodies one skilled in the art will be able to determine a suitable method for linking a given agent to an antibody.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Epitope: A site on an antigen recognized by an antibody, as determined by the specificity of the antibody amino acid sequence. Epitopes are also called antigenic determinants.

Framework Region: Amino acid sequences interposed between CDRs. Antibody framework region includes variable light and variable heavy framework regions. The framework regions serve to hold the CDRs in an appropriate orientation for antigen binding. The numbering of the residues in the light chain and heavy chain framework regions follows the numbering convention delineated by Kabat et al., (1991, supra).

High binding affinity: Affinity of an antibody for an antigen where the relative affinity of the humanized CC49 antibody is similar or increased as compared to that of a parent CC49 antibody, for example HuCC49V10. In one embodiment, affinity is calculated by a modification of the Scatchard method described by Frankel et al., *Mol. Immunol.*, 16:101-106, 1979. One of skill in the art can readily identify a statistical test that determines a statistically significant result, for example, the Student's t-test, the Wilcoxon two sample test, or the Median test. In one embodiment, the humanized CC49 antibody has a high binding affinity for TAG-72 that is at least about $0.6 \times 10^{-8}$ M. In other embodiments, the humanized CC49 antibody has a high binding affinity for TAG-72 that is at least about $1.0 \times 10^{-8}$, about $1.2 \times 10^{-8}$, about $1.5 \times 10^{-8}$, about $2.0 \times 10^{-8}$, about $2.5 \times 10^{-8}$, about $3.0 \times 10^{-8}$, about $3.5 \times 10^{-8}$, about $4.0 \times 10^{-8}$, about $4.5 \times 10^{-8}$, or about $5.0 \times 10^{-8}$ M.

In another embodiment, a high binding affinity is measured by an antigen/antibody dissociation rate of a humanized CC49 antibody that is significantly lower than the parent antibody. In yet another embodiment, a high binding affinity is measured by a competition radioimmunoassay, where the amount of antibody needed for 50% inhibition of the binding of $^{125}$I-labeled HuCC49 antibody to BSM is less than that required by the parent CC49 antibody. In another embodiment, a high binding affinity is measured by flow cytometry as an increased number of gated cells labeled with humanized CC49 antibody compared to the number of cells labeled by the parent CC49 antibody.

HAMA (Human anti-murine antibody) response: An immune response in a human subject to the variable and constant regions of a murine antibody that has been administered to the subject. Repeated antibody administration may lead to an increased rate of clearance of the antibody from the patient's serum and may also elicit allergic reactions in the subject.

Humanized antibody: A human antibody genetically engineered to include mouse hypervariable regions, CDRs and/or SDRs. In one embodiment, the DNA encoding hypervariable loops of mouse monoclonal antibodies or variable regions selected in phage display libraries is inserted into the framework regions of human Ig genes. Antibodies can be "customized" to have a desired binding affinity or to be minimally immunogenic in the humans treated with them.

Humanized CC49 antibodies: CC49 antibodies humanized by grafting CC49 CDRs (Kashmiri et al., *Hybridoma*, 14: 461-473, 1995) or SDRs (Tamura et al., *J. Immunol.* 164:

1432-1441, 2000; WO 00/26394) onto the frameworks of the relevant human antibodies. CC49 CDRs include synthetic amino acid sequences that are identical in sequence to the CC49 CDRs. CC49 can be humanized by grafting only CC49 CDRs that are important for antigen binding onto the variable light and variable heavy framework regions of, for example, LEN and 21/28'CL human antibodies and additionally replacing non-specificity determining residues (SDRs) in the murine CDRs with the corresponding residue in the human antibody. A limited number of murine framework residues, can be included in a humanized antibody. In one embodiment, no murine resides are included in the framework region. In other embodiments, at most about one, two, three four, five, six, seven, eight, nine, ten, twelve, fourteen, fifteen, or sixteen murine amino acids are included in the human framework. A specific humanized CC49 antibody, termed HuCC49 has been deposited with ATCC as HB-12404.

The variant HuCC49V10 carries the L-CDR-1 and L-CDR2 of the human antibody LEN, and a threonine at position 97 in the CC49 L-CDR3 is replaced with a serine residue present at the corresponding position in the human antibody LEN. The variant HuCC49V10 also has several substitutions in the heavy chain. Specifically, an asparagine at position 60 in the murine CC49 H-CDR2 is replaced with a serine, a glutamic acid at position 61 in the murine CC49 H-CDR2 is replaced with a glutamine, an arginine at position 62 in the murine CC49 H-CDR2 is replaced with a lysine, and a lysine at position 64 in the murine CC49 H-CDR2 is replaced with a glutamine. It should be noted that HuCC49V10 is described in US. patent application Ser. No. 09/830,748 (now U.S. Pat. No. 6,818,749) and PCT Publication No. WO 00/26394, both of which are incorporated herein by reference. HuCC49V10 was deposited with American Type Culture Collection, 10801 University Boulevard, Manassas, Va. 20110-2209, on Aug. 28, 2003, and has ATCC Accession No. PTA-5416. For the purposes of this disclosure, HuCC49V10 can be referred to as the parental antibody.

Additional humanized CC49 antibodies are HuCC49V10$^{-14}$ (ATCC Accession No. PTA-4182, also termed HuCC49V14) and HuCC49V10-15 (ATCC Accession No. PTA-4183, also termed HuCC49V15).

Other specific, non-limiting examples of a humanized CC49 monoclonal antibody are HuCC49V10 variants V35, V37, V40, V41, V47, V48, V58, and V59. Antibody V59 was deposited with ATCC on Aug. 28, 2003, and has ATCC Accession No. PTA-5415. Methods for making these antibodies, and the amino acid sequence of the VL and VH chains of these antibodies are provided herein.

Idiotype: The property of a group of antibodies or T cell receptors defined by their sharing a particular idiotope (an antigenic determinant on the variable region); for instance, antibodies that share a particular idiotope belong to the same idiotype.

"Idiotype" may be used to describe the collection of idiotopes expressed by an Ig molecule. An "anti-idiotype" antibody may be prepared to a monoclonal antibody by methods known to those of skill in the art and may be used to prepare pharmaceutical compositions.

Immune cell: Any cell involved in a host defense mechanism. These can include, for example, T cells, B cells, natural killer cells, neutrophils, mast cells, macrophages, antigen-presenting cells, basophils, eosinophils, and neutrophils.

Immune response: A response of a cell of the immune system, such as a neutrophil, a B cell, or a T cell, to a stimulus. In one embodiment, the response is specific for a particular antigen (an "antigen-specific response"). In another embodiment, the response is against an antibody, such as a HAMA response, including an anti-variable region response.

Immunogenicity: A measure of the ability of a targeting protein or therapeutic moiety to elicit an immune response (humoral or cellular) when administered to a subject.

In one example, a variant, such as, but not limited to, V59, has minimal immunogenicity (compared to the parental HuCC49V10 antibody). In one example a reduced or minimal immunogenicity, as compared to a parental antibody, is an $IC_{50}$ value for serum EA is at least about a 2-fold, 5-fold, 10-fold, 20-fold, 25-fold, 30-fold, or 35-fold higher than that of a parental antibody. However, other assays can be used to measure immunogenicity.

Immunoreactivity: A measure of the ability of an Ig to recognize and bind to a specific antigen.

Isolated: An biological component (such as a nucleic acid, peptide or protein) that has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

Ligand contact residue or Specificity Determining Residue (SDR): A residue within a CDR that is involved in contact with a ligand or antigen. A ligand contact residue is also known as a specificity determining residue (SDR). A non-ligand contact residue is a residue in a CDR that does not contact a ligand. A non-ligand contact residue can also be a framework residue.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Minimally immunogenic: An antibody that generates a reduced, for example low, immune response when administered to a subject, such as a human subject. In one embodiment, immunogenicity is measured in a competitive binding assay. In one specific, non-limiting example, immunogenicity is the ability of a variant HuCC49 antibody to prevent a parental HuCC49V10 antibody from binding to CC49 anti-idiotypic antibodies in a patient's serum. For example, if a variant HuCC49 antibody competes with an equal molar amount of the parental HuCC49V10 antibody (i.e. elicits greater than about 50% inhibition of parental HuCC49V10 binding to anti-idiotypic antibodies in a patient's serum) then the variant HuCC49 antibody is immunogenic. In another example, if a variant HuCC49 antibody competes poorly with an equal molar or less amount of the parental HuCC49V10 antibody (i.e. elicits about 50% or less inhibition of parental HuCC49V10 binding to anti-idiotypic antibodies in a patient's serum) then the variant HuCC49 antibody is minimally immunogenic. In another embodiment, if a five-fold or greater molar concentration of a variant HuCC49 antibody is required to achieve about 50% inhibition of binding of the parental antibody to its cognate anti-idiotypic antibodies present in a subject's sera, then the variant antibody is minimally immunogenic.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear single-stranded polynucleotide sequence of up to about 200 nucleotide bases in length, for example a polymer of deoxyribonucleotides or ribonucleotides which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

A "therapeutically effective amount" is a quantity of a specific substance sufficient to achieve a desired effect in a subject being treated. For instance, this can be the amount necessary to inhibit or suppress growth of a tumor or to decrease a sign or symptom of the tumor in the subject. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15$^{th}$ Edition (1975), describes compositions and formulations suitable for pharmaceutical delivery of humanized CC49 monoclonal antibodies disclosed herein.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A single-stranded linear nucleotide sequence, including sequences of greater than 100 nucleotide bases in length.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, for example, phenylalanine, is substituted for (or by) one not having a side chain, for example, glycine; or (d) a residue having an electropositive side chain, for example, lysyl, arginyl, or histadyl, is substituted for (or by) an electronegative residue, for example, glutamyl or aspartyl.

Variant amino acid sequences can be, for example, be 80%, 90% or even 95% or 98% identical to the native amino acid sequence. Programs and algorithms for determining percentage identity can be found at the NCBI website.

Preventing or treating a disease: Preventing a disease refers to inhibiting completely or in part the development or progression of a disease, for example in a person who is known to have a predisposition to a disease, such as colorectal cancer, breast, ovarian, or prostate cancer. An example of a person with a known predisposition is someone with a history of cancer in the family, or who has been exposed to factors that predispose the subject to the development of a tumor. Treating a disease refers to a therapeutic intervention that inhibits, or suppresses the growth of a tumor, eliminates a tumor, ameliorates at least one sign or symptom of a disease or pathological condition, or interferes with a pathophysiological process, after the disease or pathological condition has begun to develop.

Protein: A biological molecule encoded by a gene and comprised of amino acids.

Recombinant: A recombinant nucleic acid is one that has a sequence that is not naturally occurring or was made artificially. Artificial combination is often accomplished by chemical synthesis or, more commonly, by the artificial manipulation of isolated segments of nucleic acids, for example, by genetic engineering techniques. Similarly, a recombinant protein is one encoded by a recombinant nucleic acid molecule.

Selectively hybridize: Hybridization under moderately or highly stringent conditions that excludes non-related nucleotide sequences.

In nucleic acid hybridization reactions, the conditions used to achieve a particular level of stringency, will vary depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (for example, *Molecular Cloning: A Laboratory Manual*, 2nd ed., vol. 1-3, ed. Sambrook et al., Cold Spring Harbor Laboratory Press, Cold Spring Harbor, N.Y., 2001). Washing can be carried out using only one of these conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Subject: Living multi-cellular vertebrate organisms, a category that includes both human and non-human mammals.

TAG (Tumor-Associated Glycoprotein)-72: A cell-surface glycoprotein that is expressed on human carcinomas, including adenocarcinoma, colorectal, gastric, pancreatic, breast, lung and ovarian carcinomas. TAG-72 has a high molecular weight (greater than $1 \times 10^6$) as measured by size-exclusion chromatography, a density of 1.45 g/ml, is resistant to Chondroitinase digestion, expresses blood group-related oligosaccharides, and is heavily sialylated with O-glycosidically linked oligosaccharides characteristic of mucins. These characteristics suggest that TAG-72 is a mucin-like molecule (Johnson et al., *Cancer Res.* 46:850-857, 1986, incorporated herein by reference).

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Treatment: Refers to both prophylactic inhibition of initial infection or disease, and therapeutic interventions to alter the natural course of an untreated infection or disease process, such as a tumor growth or an infection with a bacteria.

Tumor: A neoplasm that may be either malignant or non-malignant. Tumors of the same tissue type are primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular. In one embodiment, cells in a tumor express TAG-72.

Variable region (also variable domain or V domain): The regions of both the light chain and the heavy chain of an Ig that contain antigen-binding sites. The regions are composed of polypeptide chains containing four relatively invariant "framework regions" (FRs) and three highly variant "hyper-variable regions" (HVs). Because the HVs constitute the binding site for antigen(s) and determine specificity by forming a surface complementarity to the antigen, they are more commonly termed the "complementarity-determining regions," or CDRs, and are denoted CDR1, CDR2, and CDR3. Because both of the CDRs from the heavy and light chain domains contribute to the antigen-binding site, it is the three-dimensional configuration of the heavy and the light chains that determines the final antigen specificity.

Within the heavy and light chain, the framework regions surround the CDRs. Proceeding from the N-terminus of a heavy or light chain, the order of regions is: FR1-CDR1-FR2-CDR2-FR3-CDR3-FR4. As used herein, the term "variable region" is intended to encompass a complete set of four framework regions and three complementarity-determining regions. Thus, a sequence encoding a "variable region" would provide the sequence of a complete set of four framework regions and three complementarity-determining regions.

Variant humanized CC49 antibody: A humanized CC49 antibody that has at least one amino acid substitution of a murine residue, and specifically binds TAG-72. A humanized CC49 antibody can have at most 2, at most 3, at most 4, at most 5, at most 7, at most 9, at most 10, at most 12, at most 14, at most 16, or more amino acid substitutions. In one embodiment, a variant humanized CC49 antibody is a variant of HuCC49V10. Specific non-limiting examples of variant humanized CC49 antibodies include V35, V37, V40, V41, V47, V48, V58, and V59.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Minimally Immunogenic Variants of Humanized CC49 V10

The majority of patients treated with murine CC49 (mCC49) monoclonal antibody generate HAMA responses (Divgi et al., *J Nucl Med* 36:586-592, 1995; Divgi et al., *Clin Cancer Res* 1:1503-1510, 1995; Macey et al., *Clin Cancer Res* 3:1547-1555, 1997; Rucker et al., *J Immunother* 22:80-4, 1999; Slovin et al., *Clin Cancer Res* 4:643-651, 1998; Tempero et al., *J Clin Oncol* 15:1518-1528, 1997), preventing repeated administration of the monoclonal antibody. To circumvent this problem, a humanized CC49 (HuCC49) was developed by the conventional approach of grafting all six (three heavy chain and three light chain) mCC49 CDRs onto the $V_L$ and $V_H$ frameworks of the human Abs LEN and 21/28'CL, respectively, while retaining murine framework residues that may be required for the integrity of the antigen combining site structure (FIG. 9; Kashmiri et al., *Hybridoma*, 14:461-473, 1995; see also U.S. Pat. No. 6,495,137, incorporated herein by reference). The resulting HuCC49, which shows no evidence of patients' antibody response after one injection (Forero et al., *Cancer Biotherapy & Radiopharmaceuticals*, 2002), retains its specificity to TAG-72, showing only 2- to 3-fold lower affinity than that of mCC49. HuCC49 was deposited with ATCC and has ATCC Accession No. HB-12404. However, an immune response to the variable (V) region can still develop.

To minimize any possible anti-V region antibody response that could still be evoked in patients by HuCC49, mCC49 was humanized by SDR grafting (Tamura et al., *J Immunol* 164: 1432-1441, 2000). In the SDR-grafted HuCC49V10 (V10), referred to as the parental antibody in this disclosure, the light chain L-CDR1 and L-CDR2 of CC49 were replaced with their counterparts from the human antibody LEN. The murine residue at position 97 of L-CDR3 (threonine) also was replaced with the residue located at the corresponding position in the human antibody (serine). The variant HuCC49V10 also has several substitutions in the heavy chain. Specifically, an asparagine at position 60 in the murine CC49H-CDR2 is replaced with a serine, a glutamic acid at position 61 in the murine CC49H-CDR2 is replaced with a glutamine, an arginine at position 62 in the murine CC49H-CDR2 is replaced with a lysine, and a lysine at position 64 in the murine CC49H-CDR2 is replaced with a glutamine. These substitutions are shown in Table I, below. Murine framework residues that were presumed to be indispensable for maintaining the integrity of the antibody-combining site were retained during the generation of V10. In HuCC49V10, murine CC49 framework residues were retained at positions 5, 19, 21, 43, 78, 100 and 106 of the light chain and at positions 12, 20, 38, 40, 48, 66, 67, 69, 71, 80, 91 and 93 of the heavy chain (following the numbering convention delineated by Kabat et al., 1991, supra). Compared to the CDR-grafted HuCC49, the V10 antibody shows only a 2- to 3-fold reduction in its binding affinity to the TAG-72 antigen.

In vitro sera reactivity studies reveal that compared to HuCC49, V10 shows a dramatic decrease in its reactivity to the anti-V region Abs present in the sera of patients who were administered $^{177}$Lu-labeled mCC49 in a phase I clinical trial (Gonzales et al., *J Immunol Methods* 268:197-210, 2002; Tamura et al., *J Immunol* 164:1432-1441, 2000). Using a surface plasmon resonance (SPR)-based competition assay to measure sera reactivity, it has been shown that compared to HuCC49, V10 displays 10- to 300- fold lower reactivity to the sera of several patients (Gonzales et al., *J Immunol Methods* 268:197-210, 2002). Although SDR grafting of mCC49 has rendered V10 minimally reactive to sera from patients who had earlier been administered mCC49 in clinical trials, the recipient of V10 can still elicit an anti-V region response against the potentially immunogenic murine framework residues that were retained for their presumed indispensability in maintaining the integrity of the Ab combining site (Kashmiri et al., *Hybridoma* 14:461-473, 1995; Tamura et al., *J Immunol* 164:1432-1441, 2000). It should be noted that HuCC49V10 is described in U.S. patent application Ser. No. 09/830,748 (now U.S. Pat. No. 6,818,749) and PCT Publication No. WO 00/26394, both of which are incorporated herein by reference. These documents also disclose the amino acid sequence of LEN and 21/28'CL. HuCC49V10 was deposited with American Type Culture Collection, 10801 University Boulevard, Manassas, Va. 20110-2209, and has ATCC Accession No. PTA-5416.

The antibodies disclosed herein include the CDRs from HuCC49V10 (shown in Table I, below, and in FIG. 9) in a human framework. However, the antibody can also include a non-conservative substitution at position 91 of HuCC49V10 LCDR3 (SEQ ID NO: 11), such as a tyrosine to proline substitution (HuCC49V10-14; see U.S. Patent Application No. 60/393,077, now U.S. Pat. No. 6,818,749, and PCT patent application Ser. No. PCT/US03/20367, filed Jun. 26, 2003, both of which are incorporated herein by reference). Alternatively, the antibody can have a leucine at position 27b of HuCC49V10 LCDR1 (SEQ ID NO: 9) and a non conservative amino acid substitution at position 91 of HuCC49V10 LCDR3 (SEQ ID NO: 11), such as a proline at position 91 (HuCC49V10-15; see U.S. Patent Application No. 60/393, 077 and PCT patent application Ser. No. PCT/US03/20367, filed Jun. 26, 2003, both of which are incorporated herein by reference.

TABLE I

Light and Heavy Chain CDR Sequences of HuCC49 and HuCC49V10

Light chain

| | | | | | | | | | | | | | | | | | | |
|---|---|---|---|---|---|---|---|---|---|---|---|---|---|---|---|---|---|---|
| CDR1 | 24[1] | 25 | 26 | 27 | a | b | c | d2 | e | f | 28 | 29 | 30 | 31 | 32 | 33 | 34 |
| HuCC49 (SEQ ID NO: 31) | Lys | Ser | Ser | Gln | Ser | Leu | Leu | Tyr | Ser | Gly | Asn | Gln | Lys | Asn | Tyr | Leu | Ala |
| V10[3] (SEQ ID NO: 9) | Lys | Ser | Ser | Gln | Ser | VAL4 | Leu | Tyr | Ser | SER | Asn | SER | Lys | Asn | Tyr | Leu | Ala |

| | | | | | | | |
|---|---|---|---|---|---|---|---|
| CDR2 | 50 | 51 | 52 | 53 | 54 | 55 | 56 |
| HuCC49 (SEQ ID NO: 32) | Trp | Ala | Ser | Ala | Arg | Glu | Ser |
| V10 (SEQ ID NO: 10) | Trp | Ala | Ser | THR | Arg | Glu | Ser |

TABLE I-continued

Light and Heavy Chain CDR Sequences of HuCC49 and HuCC49V10

| | 89 | 90 | 91 | 92 | 93 | 94 | 95 | 96 | 97 | | | | | | | |
|---|---|---|---|---|---|---|---|---|---|---|---|---|---|---|---|---|
| CDR3 | | | | | | | | | | | | | | | | |
| HuCC49 (SEQ ID NO: 33) | Gln | Gln | Tyr | Tyr | Ser | Tyr | Pro | Leu | Thr | | | | | | | |
| V10 (SEQ ID NO: 11) | Gln | Gln | Tyr | Tyr | Ser | Tyr | Pro | Leu | SER | | | | | | | |

Heavy chain

| | 31 | 32 | 33 | 34 | 35 | | | | | | | | | | | |
|---|---|---|---|---|---|---|---|---|---|---|---|---|---|---|---|---|
| CDR1 | | | | | | | | | | | | | | | | |
| HuCC49 (SEQ ID NO: 34) | Asp | His | Ala | Ile | His | | | | | | | | | | | |
| V10 (SEQ ID NO: 12) | Asp | His | Ala | Ile | His | | | | | | | | | | | |

| | 50 | 51 | 52 | a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| CDR2 | | | | | | | | | | | | | | | | | |
| HuCC49 (SEQ ID NO: 35) | Tyr | Phe | Ser | Pro | Gly | Asn | Asp | Asp | Phe | Lys | Tyr | Asn | Glu | Arg | Phe | Lys | Gly |
| V10 (SEQ ID NO: 13) | Tyr | Phe | Ser | Pro | Gly | Asn | Asp | Asp | Phe | Lys | Tyr | SER | GLN | LYS | Phe | GLN | Gly |

| | 95 | 96 | 97 | 98 | 99 | 100 | a | b | 101 | 102 |
|---|---|---|---|---|---|---|---|---|---|---|
| CDR3 | | | | | | | | | | |
| HuCC49 (SEQ ID NO: 36) | Ser | Leu | Asn | Met | Ala | — | — | — | — | Tyr |
| V10 (SEQ ID NO: 14) | Ser | Leu | Asn | Met | Ala | | | | | Tyr |

¹Amino acid residues are numbered as described by Kabat.
²Residue position shown in BOLD denote the specificity-determining residues (SDRs).
³V10 represents HuCC49V10
⁴HuCC49V10 residues derived from corresponding positions of human MAbs LEN and 21/28'CL shown in ALL CAPS Thus, in one embodiment, the antibody does not include L-CDR3 from HuCC49V10, but includes L-CDR3 from HuCC49V14 (ATCC Accession No. PTA-4182). In this embodiment the L-CDR3, or SDR from HuCC49V14 L-CDR3, can be utilized. Thus, the antibodies include an L-CDR3 (or SDR from L-CDR3) from HuCC49V14, and a L-CDR1, a L-CDR2, a H-CDR-1, a H-CDR2, and a H-CDR3 from humanized antibody HuCC49V10. The L-CDR1, L-CDR2, L-CDR3 are within a HuCC49V10 light chain framework region that includes the corresponding amino acid from LEN at position 5, 19, 21, and 106 in the light chain. The H-CDR1, H-CDR2, and H-CDR3 are within a heavy chain HuCC49V10 framework comprising a corresponding human 21/28'CL residue at positions 20, 38, 48, 66, 67, 69, and 80 in the heavy chain. In one embodiment, corresponding murine CC49 framework residues are retained at positions 71, 91, 93 of the heavy chain. These humanized CC49 antibodies retain binding affinity for TAG-72 and have reduced immunogenicity, as compared to a parental HuCC49V10 antibody.

The L-CDRs from HuCC49V15 (see ATCC Accession No. PTA-4183) can also be utilized. In this embodiment, the antibody does not include L-CDR1 or L-CDR3 (or an SDR from L-CDR1 or L-CDR3) from HuCC49V10, but includes L-CDR1 and L-CDR3 (or an SDR from L-CDR1 or L-CDR3) from HuCC49V15. The antibody also includes a L-CDR2, and a HCDR1, a H-CDR2, and a H-CDR3 from humanized antibody HuCC49V10. The L-CDR1, L-CDR2, L-CDR3 are within a HuCC49V10 light chain framework region that includes the corresponding framework amino acid from LEN at position 5, 19, 21, and 106 in the light chain. The H-CDR1, H-CDR2, and H-CDR3 are within a heavy chain HuCC49V10 framework comprising a corresponding framework human 21/28'CL residue at positions 20, 38, 48, 66, 67, 69, and 80 in the heavy chain. In one embodiment, corresponding murine CC49 framework residues are retained at positions 71, 91, 93 of the heavy chain. These humanized CC49 antibodies retain binding affinity for TAG-72 and have reduced immunogenicity, as compared to a parental HuCC49V10 antibody. HuCC49V14 and HuCC49V15 have been previously disclosed (see U.S. Patent Application No. 60/393,077 and PCT Patent Application No. PCT/US03/20367, filed Jun. 26, 2003, both of which are incorporated herein by reference).

The light chain frameworks of human mAb LEN have the following sequences:

```
                                        (SEQ ID NO: 21)
    FR1: DIVMTQS PDSLAVSLGERATINC (SEQ ID NO: 22)
    FR2: WYQQKPGQPPLLIY (SEQ ID NO: 23)
    FR3: GVPDRPFGSGSGTDFTLTISSLQAEDVAVYYC (SEQ ID NO: 24)
    FR4: FGQGQTKLEIK
```

The heavy chain frameworks of human mAb 21/28' CL have the following sequences:

```
                                        (SEQ ID NO: 26)
    FR1: QVQLVQSGAEVKKPQASVKVSCKASQYTFT (SEQ ID NO: 27)
    FR2: WVRQAPGQRLEWMG
```

-continued

```
                                            (SEQ ID NO: 28)
    FR3: RVTITRDTSASTAYMELSSLRSEDTAVYYCAR (SEQ ID NO: 29)
    FR4: WGQGTLVTVSS.
```

The light chain framework regions of HuCC49V10 are listed below:

```
                                            (SEQ ID NO: 1)
    FR1: DIVMSQSPDSLAVSLGERVTLNC (SEQ ID NO: 2)
    FR2: WYQQKPGQSPKLLIY (SEQ ID NO: 3)
    FR3: GVPDRFSGSGSGTDFTLTISSVQAEDVAVYYC (SEQ ID NO: 4)
    FR4: FGAGTKLELK
```

The heavy chain framework regions of HuCC49V10 are listed below:

```
                                            (SEQ ID NO: 5)
    FR1: QVQLVQSGAEVVKPGASVKISCKASGYTFT (SEQ ID NO: 6)
    FR2: WVKQNPGQRLEWIG (SEQ ID NO: 7)
    FR3: KATLTADTSASTAYVELSSLRSEDTAVYFCTR (SEQ ID NO: 8)
    FR4: WGQGTLVTVSS
```

The antibodies disclosed herein bind TAG-72 and include the amino acid sequence of the CDRs of HuCC49V10, but include substitutions of murine residues retained in the framework of the HuCC49V10 light chain or heavy chain. Thus, the variant antibodies disclosed herein include a residue from the corresponding position in a parental human antibody at specified positions (these are specified herein using the numbering convention delineated by Kabat et al., 1991, supra). Murine framework residues retained in the light chain of HuCC49V10 are at positions 5, 19, 21, 43, 78, 100 and 106. In one embodiment, the variant HuCC49V10 antibody includes a substitution of residues 5, 19, 21 and 106 in the HuCC49V10 framework of the light chain with corresponding human residues from LEN. In one example, the antibody includes a substitution at positions 5, 19, 21, 78 and 106 (see FIG. 2, frameworks 1-4 of variant HuCC49V10 antibody V35; SEQ ID NOs: 37-40) of the framework of the light chain. In another example, the antibody includes a substitution at positions 5, 19, 21, 43, 78, 100 and 106 of the framework of the light chain (see FIG. 2, frameworks 1-4 of variant HuCC49V10 antibody V37; SEQ ID NOs: 41-44). The corresponding residues from LEN are shown in FIG. 9.

Murine framework residues retained in the heavy chain of HuCC49V10 are at positions 12, 20, 38, 40, 48, 66, 67, 69, 71, 80, 91, and 93 (following the numbering convention delineated by Kabat et al., 1991, supra). In one embodiment, the variant HuCC49V10 antibody includes substitutions of residues at positions 20, 38, 48, 66, 67, 69, and 80 in the heavy chain HuCC49V10 framework with corresponding human residues from 21/28'CL. In one example, the heavy chain framework includes the corresponding human residues at positions 20, 38, 48, 66, 67, 69, 80 (see FIG. 2, frameworks 1-4 of HuCC49V10 variant V40; SEQ ID NOs: 45-48). In another example, the heavy chain framework includes corresponding human amino acid residues at positions number 12, 20, 38, 40, 48, 66, 67, 69, 80 of the heavy chain framework (see FIG. 2, frameworks 1-4 of HuCC49V10 variant V41; SEQ ID NOs: 49-52).

One of skill in the art can readily design antibodies including one of the light chain framework regions of the variants disclosed herein (V35 and V37) and one of the heavy chain framework regions disclosed herein (V40 and V10), wherein the antibody includes the CDRs and/or SDRs from an antibody that specifically binds TAG-72, such as HuCC49V10. Specific examples of antibodies of use are disclosed herein, namely V47, V48, V58 and V59, which include one VL selected from the group consisting of V35 and V37, and one VH selected from the group consisting of V40 and V41.

For example, an antibody (V47) can be produced that includes V35 and V40. In another example, an antibody (V48) can be produced that includes V37 and V40. In yet another example, an antibody (V58) can be produced that includes V35 and V41. In a further example, an antibody (V59) can be produced that includes V37 and V41. It should be noted that all of these antibodies include the CDRs of HuCC49V10.

In one example, the antibody has a VL which includes (1) a light chain framework region including the amino acid sequences set forth as SEQ ID NOs: 41-44 and (2) L-CDRs including the amino acid sequences set forth as SEQ NOs: 9-12. The antibody also includes a VH which includes (1) heavy chain framework region including the amino acid sequences set forth as SEQ ID NOs: 49-52 and (2) H-CDRs including the amino acid sequences set forth as SEQ ID NOs: 12-14. This humanized CC49 antibody retains binding affinity for TAG-72 and has reduced immunogenicity, as compared to a parental humanized CC49 V10 antibody.

The sequence information provided herein for the light chain framework regions and the heavy chain framework regions disclosed herein can be used to produce additional antibodies, including the LCDRs and the HCDRs, or heavy and light chain SDRs, from any other antibody that specifically binds TAG-72. For example, the CDRs or SDRs from HuCC49V14 (ATCC Accession No. PTA-4182) can be utilized. The CDRs and SDRs from HuCC49V15 (ATCC Accession No. PTA-4183) can also be utilized.

The variant antibodies disclosed herein, such as V47, V48, V58 and V59, contain a reduced number of murine residues, and consequently, reduced immunogenicity, when compared to HuCC49 and HuCC49V10. Without being bound by theory, it is believed that this is due to a reduced number of amino acids that correspond to a murine antibody. Nonetheless, the variants of the invention retain a binding affinity that is similar or is increased as compared to HuCC49V10. Thus, the humanized monoclonal antibodies disclosed herein bind TAG-72 with high binding affinity. In one embodiment, the humanized CC49 antibody has a high binding affinity for TAG-72 that is at least about $0.6 \times 10^{-8}$ M. In other embodiments, the humanized CC49 antibody has a high binding affinity for TAG-72 that is at least about $1.0 \times 10^{-8}$, about $1.2 \times 10^{-8}$, about $1.5 \times 10^{-8}$, about $2.0 \times 10^{-8}$, about $2.5 \times 10^{-8}$, about $3.0 \times 10^{-8}$, about $3.5 \times 10^{-8}$, about $4.0 \times 10^{-8}$, about $4.5 \times 10^{-8}$, or about $5.0 \times 10^{-8}$ M. In one embodiment, the humanized CC49 antibody has a high binding affinity if it has a significantly lower antigen/antibody dissociation rate compared to that of the parent HuCC49V10 antibody. In another embodiment, the humanized CC49 antibody has a high binding affinity if less antibody is required for a 50% inhibition of the binding of $^{125}$I-labeled HuCC49 to BSM compared to the parent HuCC49V10 antibody. In yet another embodiment, the humanized CC49 antibody has a high binding affinity when the number of cells labeled with humanized CC49 antibody is significantly greater than the number of cells labeled by the parent HuCC49V10 antibody, as measured by flow cytometry.

Immunogenicity of variant HuCC49 antibodies can be measured in a competitive binding assay as the ability of a variant HuCC49 antibody to prevent a CC49, HuCC49 or HuCC49V10 antibody from binding to anti-idiotypic antibodies in a human subject's serum. In one embodiment, the variant antibody is minimally immunogenic in a subject. In one embodiment, at least about five-fold higher molar concentration of the variant humanized CC49 antibody, than that of the parental HuCC49V10 antibody, is required to elicit 50% inhibition of the parental HuCC49V10 binding to its cognate anti-idiotypic antibodies in a subject's sera. In other embodiments, at least about ten-fold, at least about twenty five-fold, at least about fifty-fold, at least about seventy-fold, or at least about one hundred-fold higher molar concentration of the variant humanized CC49 antibody, than that of the parental antibody HuCC49V10, is required to elicit 50% inhibition of the parental HuCC49V10 binding to its cognate anti-idiotypic antibodies in a subject's sera.

Effector molecules, for example, therapeutic, diagnostic, or detection moieties, can be linked to a variant humanized CC49 antibody that specifically binds TAG-72, using any number of means known to those of skill in the art. Thus, a variant humanized CC49 antibody with an amino acid substitution can have any one of a number of different types of effector molecules linked to it. In one embodiment, the antibody is linked to a detectable label. In some embodiments, the antibody is linked to a radioactive isotope, an enzyme substrate, a co-factor, a ligand, a chemiluminescent agent, a fluorescent agent, a hapten, or an enzyme. In another embodiment, the antibody is linked to a cytotoxin (see below). In other embodiments, the antibody is linked to a chemotherapeutic drug, a radioactive isotope, a bacterially-expressed toxin, a virally-expressed toxin, or a venom protein. In yet other embodiments, the antibody is linked to a cytokine. Specific, non-limiting examples of cytokines are IL-2, IL-4, IL-10, TNF-alpha and IFN-gamma. The antibody can be linked to an effector molecule by a covalent or non-covalent means.

Polynucleotides encoding the VL and/or the VH of humanized antibodies that bind TAG-72, such as V47, V48, V58 and V59 are also provided. These polynucleotides include DNA, cDNA and RNA sequences which encode the humanized antibody. It is understood that all polynucleotides encoding these antibodies are also included herein, as long as they encode a polypeptide with the recognized activity, such as the binding to TAG-72. The polynucleotides of this disclosure include sequences that are degenerate as a result of the genetic code. There are 20 natural amino acids, most of which are specified by more than one codon. Therefore, all degenerate nucleotide sequences are included as long as the amino acid sequence of the antibody encoded by the nucleotide sequence is functionally unchanged.

Primers, such as PCR primers, can readily be prepared that hybridize to a nucleic acid sequence encoding a specific VH or VL, or a component thereof. In one embodiment, the primers include at least ten, at least 15, 16, 17, 18, 18, or 20 consecutive nucleotides of a nucleic acid encoding the VH or VL of interest. Also included are fragments of the above-described nucleic acid sequences that are at least 15 bases in length, which is sufficient to permit the fragment to selectively hybridize to DNA that encodes the antibody of interest under physiological conditions. The term "selectively hybridize" refers to hybridization under moderately or highly stringent conditions, which excludes non-related nucleotide sequences.

A nucleic acid encoding a VL and/or VH of a humanized antibody that specifically binds TAG-72 can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N.Y., 1989). Polynucleotides also can be isolated by screening genomic or cDNA libraries with probes selected from the sequences of the desired polynucleotide under stringent hybridization conditions.

The polynucleotides include a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides of the invention can be ribonucleotides, deoxyribonucleotides, or modified forms of either nucleotide. The term includes single and double forms of DNA.

DNA sequences encoding a VL and/or VH of a humanized antibody that specifically binds TAG-72 can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding a VL and/or VH of a humanized antibody that specifically binds TAG-72 can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (for instance, ATG) in front of a protein-encoding gene, splicing signal for introns, maintenance of the correct reading frame of that gene to permit proper translation of mRNA, and stop codons.

The polynucleotide sequences encoding a VL and/or VH of a humanized antibody that specifically binds TAG-72 can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitation, conventional mechanical procedures such as microinjection, electroporation, insertion of a plasmid encased in liposomes, or virus vectors may be used. Eukaryotic cells can also be cotransformed with the polynucleotide sequence of interest, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of recombinantly expressed polypeptides may be carried out by conventional means including preparative chromatography and immunological separations.

Pharmaceutical Compositions and Therapeutic Methods

Pharmaceutical compositions are disclosed herein that include a humanized CC49 monoclonal antibody, such as V47, V48, V58 or V59, that can be formulated with an appropriate solid or liquid carrier, depending upon the particular mode of administration chosen. In addition, a humanized CC49 monoclonal antibody linked to an effector molecule (for instance, toxin, chemotherapeutic drug, or detectable label) can be prepared in pharmaceutical compositions.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate. Actual methods for preparing administrable compositions will be known or apparent to those skilled in the art and are described in more detail in such publications as Remingtons Pharmaceutical Sciences, 19$^{th}$ Ed., Mack Publishing Company, Easton, Pa. (1995).

The dosage form of the pharmaceutical composition will be determined by the mode of administration chosen. For instance, in addition to injectable fluids, topical, inhalation, oral and suppository formulations can be employed. Topical preparations can include eye drops, ointments, sprays and the like. Inhalation preparations can be liquid (for example, solutions or suspensions) and include mists, sprays and the like. Oral formulations can be liquid (for example, syrups, solutions or suspensions), or solid (for example, powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a humanized CC49 monoclonal antibody, such as V47, V48, V58 or V59, can be formulated in unit dosage form, suitable for individual administration of precise dosages. In addition, the pharmaceutical compositions may be administered as an immunoprophylactic in a single dose schedule or as an immunotherapy in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner. In one specific, non-limiting example, a unit dosage can be about 0.1 to about 10 mg per patient per day. Dosages from about 0.1 up to about 100 mg per patient per day may be used, particularly if the agent is administered to a secluded site and not into the circulatory or lymph system, such as into a body cavity, into a lumen of an organ, or directly into a tumor. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (for example, the subject, the disease, the disease state involved, and whether the treatment is prophylactic).

In one embodiment, a therapeutically effective amount of a humanized CC49 antibody, such as V47, V48, V58 or V59, is the amount of humanized CC49 antibody necessary to inhibit further growth of a TAG-72-expressing tumor or suppress the growth of a TAG-72-expressing tumor, without eliciting a HAMA response in the patient receiving the treatment. In other embodiments, a therapeutically effective amount of humanized CC49 antibody is the amount of humanized CC49 antibody necessary to eliminate or reduce the size of a TAG-72-expressing tumor, without eliciting a HAMA response. Specific, non-limiting examples of TAG-72-expressing tumors are adenocarcinoma, colorectal, gastric, pancreatic, breast, lung, and ovarian tumors. In yet another embodiment, a therapeutically effective amount of humanized CC49 antibody is an amount of humanized CC49 antibody that is effective at reducing a sign or a symptom of the tumor and induces a minimal HAMA response.

A therapeutically effective amount of a humanized CC49 monoclonal antibody, such as V47, V48, V58 or V59, can be administered in a single dose, or in several doses, for example daily, during a course of treatment. In one embodiment, treatment continues until a therapeutic result is achieved. However, the effective amount of humanized CC49 antibody will be dependent on the subject being treated, the severity and type of the affliction, and the manner of administration of the therapeutic(s).

Controlled release parenteral formulations of a humanized CC49 monoclonal antibody can be made as implants, oily injections, or as particulate systems. For a broad overview of protein delivery systems (see Banga, A. J., *Therapeutic Peptides and Proteins: Formulation, Processing, and Delivery Systems*, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837,028; 4,957,735 and 5,019,369; 5,055,303; 5,514,670; 5,413,797; 5,268,164; 5,004,697; 4,902,505; 5,506,206, 5,271,961; 5,254,342 and 5,534,496).

Site-specific administration of the disclosed compounds can be used, for instance by applying the humanized CC49 antibody to a pre-cancerous region, a region of tissue from which a tumor has been removed, or a region suspected of being prone to tumor development. In some embodiments, sustained intra-tumoral (or near-tumoral) release of the pharmaceutical preparation that includes a therapeutically effective amount of humanized CC49 antibody may be beneficial.

The present disclosure also includes therapeutic uses of variant humanized CC49 monoclonal antibodies, such as V47, V48, V58, or V59, that are non-covalently or covalently linked to effector molecules. In one specific embodiment, the humanized CC49 monoclonal antibody is covalently linked to an effector molecule that is toxic to a tumor or cell expressing TAG-72. In one specific, non-limiting example, the effector molecule is a toxin. In other specific, non-limiting examples, the effector molecule is a radioactive isotope, a chemotherapeutic drug, a bacterially-expressed toxin, a virally-expressed toxin, a venom protein, or a cytokine.

The cell growth inhibiting chimeric molecules include of a humanized CC49 monoclonal antibody, such as V47, V48, V58 or V59, linked to a toxin. This molecule can be prepared in pharmaceutical compositions. Toxins can be employed with antibodies that specifically bind TAG-72 to yield immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095, 1988; and Olsnes, *Methods Enzymol.* 50:330-335, 1978).

In several embodiments, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL and REDL. See Siegall et al., *J. Biol. Chem.* 264: 14256, 1989. In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided as SEQ ID NO: 1 of commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall et al., *J. Biol. Chem.* 264:14256-14261, 1989, incorporated by reference herein.

PE employed includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (for example, as a protein or pre-protein). Cytotoxic fragments of PE include PE40, PE38, PE37, and PE35. PE40 is a truncated derivative of PE as previously described in the art. See, Pai et al., *Proc. Nat'l Acad. Sci. USA* 88:3358-

62, 1991; and Kondo et al., *J. Biol. Chem.* 263:9470-9475, 1988. PE35 is a 35 kD carboxyl-terminal fragment of PE composed of a methionine at position 280 followed by amino acids 281-364 and 381-613 of native PE. PE37, another truncated derivative of PE, is described in U.S. Pat. No. 5,821, 238. PE38 is a truncated PE pro-protein composed of amino acids 253-364 and 381-613 which is activated to its cytotoxic form upon processing within a cell (see U.S. Pat. No. 5,608, 039, incorporated herein by reference). In a particularly preferred embodiment, PE38 is the toxic moiety of the immunotoxin, however, other cytotoxic fragments, such as PE35, PE37, and PE40, are contemplated and are disclosed in U.S. Pat. Nos. 5,602,095; 5,821,238; and 4,892,827, each of which is incorporated herein by reference.

Monoclonal antibodies covalently linked to an effector molecule have a variety of uses. For example, a humanized CC49 antibody such as V47, V48, V58 or V59 can be linked to a radioactive isotope and used in immunotherapy. A humanized CC49 antibody covalently linked to a radioactive isotope is of use to localize a tumor in radioimmunoguided surgery, such that the tumor can be removed. In one embodiment, about 10 mCi of a radiolabeled humanized CC49 monoclonal antibody is administered to a subject. In other embodiments, about 15 mCi, about 20 mCi, about 50 mCi, about 75 mCi or about 100 mCi of a radiolabeled humanized CC49 monoclonal antibody is administered to a subject.

The present disclosure also includes combinations of a humanized CC49 monoclonal antibody, such as V47, V48, V58 or V59, with one or more other agents useful in the treatment of tumors. For example, the compounds of this disclosure can be administered in combination with effective doses of immunostimulants, anti-cancer agents, anti-inflammatory agents, anti-infectives, and/or vaccines. The term "administration in combination" or "co-administration" refers to both concurrent and sequential administration of the active agents. A subject that is suffering from a tumor, or is predisposed to the development of a tumor, will be a candidate for treatment using the therapeutic methods disclosed herein.

Diagnostic Methods and Kits

A method is provided herein for the in vivo or in vitro detection of TAG-72-expressing tumors or cells. An in vivo detection method can localize any tumor or cell that expresses TAG-72 in a subject. In one embodiment, a diagnostically effective amount of a humanized CC49 antibody such as V47, V48, V58 or V59 is administered to the subject for a sufficient amount of time for the antibody to localize to the tumor or cell in the subject and to form an immune complex with TAG-72. The immune complex is then detected. In one specific, non-limiting example detection of an immune complex is performed by immunoscintography. Other specific, non-limiting examples of immune complex detection include radiolocalization, radioimaging, or fluorescence imaging.

In one example, the antibody is directly linked to an effector molecule that is a detectable label. Specific, non-limiting examples of detectable labels include a radioactive isotope, an enzyme substrate, a co-factor, a ligand, a chemiluminescent agent, a fluorescent agent, a hapten, or an enzyme.

In another example, a diagnostically effective amount of a humanized CC49 antibody and a secondary antibody are administered to the subject for a sufficient amount of time for the humanized CC49 antibody to form an immune complex with TAG-72 on a tumor or cell, and for the secondary antibody to form an immune complex with the humanized CC49 antibody. In one embodiment, the humanized CC49 antibody is complexed with the secondary antibody prior to their administration to the subject. In one specific, non-limiting embodiment, the secondary antibody is linked to a detectable label. In one embodiment, the immune complex, which includes TAG-72, the humanized CC49 antibody, and the secondary antibody linked to a detectable label, is detected as described above.

A method of detecting tumors in a subject includes the administration of a diagnostically effective amount of a humanized CC49 antibody such as V47, V48, V58 or V59 complexed to an effector molecule, such as a radioactive isotope. After a sufficient amount of time has elapsed to allow for the administered radiolabeled antibody to localize to the tumor, the tumor is detected. In one specific, non-limiting example, a radiolabeled immune complex is detected using a hand held gamma detection probe. Primary tumors, metastasized tumors or cells expressing TAG-72 can be detected.

For example, a humanized CC49 antibody complexed to an effector molecule, such as a radioactive isotope, is administered to a subject prior to surgery or treatment. In one specific embodiment, the detection step is performed prior to surgery to localize the tumor. In another embodiment, the detection step is performed during surgery, for example to detect the location of the tumor prior to removing it, as in radioimmunoguided surgery. A humanized CC49 antibody complexed to an effector molecule, such as a radioactive isotope, can also be administered to a subject following surgery or treatment, to determine the effectiveness of the treatment, such as to ensure the complete removal of the tumor, or to detect a recurrence of the tumor.

In vitro detection methods are provided herein. These methods can be used to screen any biological sample to assess for the presence of a tumor or cell that expresses TAG-72. A biological sample can be obtained from a mammal, such as a human, suspected of having a tumor expressing TAG-72. In one embodiment the subject has a colorectal tumor. In other embodiments, the subject has a gastric tumor, a pancreatic tumor, a breast tumor, a lung tumor, an adenocarcinoma, or an ovarian tumor. Other biological samples that can be detected by the in vitro detection method include samples of cultured cells that express TAG-72.

Such samples include, but are not limited to, tissue from biopsies, autopsies, and pathology specimens. Biological samples also include sections of tissues, such as frozen sections taken for histological purposes. Biological samples further include body fluids, such as blood, serum, saliva, or urine.

A kit is provided herein for detecting a TAG-72-expressing tumor or cell. Kits for detecting a TAG-72-expressing tumor or cell will typically include a humanized CC49 antibody that specifically binds TAG-72, such as one or more of V47, V48, V58 or V59. An antibody fragment, such as an Fv fragment can be included in the kit. The antibody can also be provided as an immunoconjugate. Thus, in several examples, the antibody is conjugated to a detectable label, such as a radioactive isotope, an enzyme substrate, a co-factor, a ligand, a fluorescent agent, a hapten, an enzyme, or a chemiluminescent agent.

The kit can further include instructional materials disclosing means of use of an antibody that specifically binds TAG-72, such as V47, V48, V58 or V59, or a fragment thereof. The instructional materials may be written, in an electronic form (for example, computer diskette or compact disk) or may be visual (for example, video files). The kits can also include additional components to facilitate the particular application for which the kit is designed. Thus, for example, the kit may additionally contain a means of detecting a label (for example, enzyme substrates for enzymatic labels, filter sets to detect fluorescent labels, appropriate secondary labels such as a secondary antibody, or the like). In one example, the kit contains a secondary antibody that is conjugated to a detectable label. Kits can additionally include buffers and other reagents, such as an antigen (for example, purified TAG-72) routinely used for the practice of a particular method, or of use in the preparation of a suitable control. Such kits and appropriate contents are well known to those of skill in the art.

The disclosure is illustrated by the following non-limiting Examples.

EXAMPLES

Example 1

Methods Used to Generate Variant HuCC49V10 Antibodies

In the experiments disclosed herein, the dispensability of some of the murine framework residues that were deemed crucial and consequently retained in HuCC49V10 (V10) has been tested. Several new variants of V10 were generated by replacing, using site-specific mutagenesis, some of the murine framework residues with their counterparts in the human templates. The variants were tested for their (a) Ag-binding reactivity and (b) reactivity to Abs in sera from patients who had earlier been administered mCC49. One such variant, V59, contains only three murine residues in its $V_L$ and $V_H$ frameworks versus 19 murine residues present in the parental Ab V10. Compared with V10, V59 shows a significantly lower reactivity to the anti-V region antibodies present in the patients' sera, while its Ag-binding affinity is unexpectedly comparable to that of the parental antibody. mAb V59 exhibits low sera reactivity and is therefore a more useful clinical reagent against human carcinomas than its predecessors. Thus, as disclosed herein, humanization of an Ab can be experimentally optimized, in terms of maintaining Ag binding and minimizing immunogenicity, by the judicious manipulation of framework residues.

The following methods were used in the experimental studies:

Synthetic oligonucleotides: Oligonucleotide primers listed below were used for the site-specific mutagenesis of the $V_L$ and $V_H$ domains of the Ab V10. V10 is described in U.S. patent application Ser. No. 09/830,748, filed Apr. 30, 2001, now U.S. Pat. No. 6,818,749,(herein incorporated by reference). V10 has been deposited with American Type Culture Collection, 10801 University Boulevard, Manassas, Va. 20110-2209, on Aug. 28, 2003 and has ATCC Accession No. PTA-5416. They were supplied by Gene Probe Technologies (Gaithersburg, Md.), but could be obtained from a variety of commercial sources. The mutagenic bases are underlined, the positions of the residue changes are parenthetically enclosed, and the sequences recognized by restriction endonucleases are in bold italics.

$V_L$ Primers:

3' VL (5):
(SEQ ID NO: 53)
5'-GTCTGGAGACTGGGTCATCACGATG-3'

3' VL (19, 21):
(SEQ ID NO: 54)
5'-GGACTTGCAATTGATAGTGGCCCTCTCGCC-3'

5' VH (43):
(SEQ ID NO: 55)
5'-CCAGGGCAGCCTCCTAAACTGCTG-3'

3' VL (43):
(SEQ ID NO: 56)
5'-CAGCAGTTTAGGAGGCTGCCCTGG-3'

5' VH (78):
(SEQ ID NO: 57)
5'-CAATCAGCAGCCTGCAGGCAGAAG-3'

3' VL (106):
(SEQ ID NO: 58)
5'GCAG*CCGCGG*CCCGTTTGATTTCCAGCTTGGTGCC-3'

3' VL (100):
(SEQ ID NO: 59)
5'-CAGCTTGGTGCCCTGGCCGAAGCTGAGG-3'

3' VL(100, 106):
(SEQ ID NO: 60)
5'-GCAG*CCGCGG*CCCGTTTGATTTCCAGCTTGGTGCCCTGGCC-3'

VH Primers:

3' VH (12):
(SEQ ID NO: 61)
5'-CCCCAGGTTTCTTCACCTCAGCGC-3'

3' VH (20):
(SEQ ID NO: 62)
5'-CCTTGCAGGACACCTTCACGGAAGC-3'

5' VH (38, 48):
(SEQ ID NO: 63)
5'CCACTGGGTGAGACAGAATCCTGGACAGCGCCTGGAGTGGATGGGATATTTCTC-3'

3' VH (38, 48):
(SEQ ID NO: 64)
5'-GAGAAATATCCCATCCACTCCAGGCGCTGTCCAGGATTCTGTCTCACCCAGTGG-3'

5' VH (40):
(SEQ ID NO: 65)
5'-GGTGAGACAGGCTCCTGGACAGC-3'

5' VH (66, 67, 69):
(SEQ ID NO: 66)
5'-GTTCCAGGGCAGGGTGACCATCACTGCAGACAC-3'

3' VH (66, 67, 69):
(SEQ ID NO: 67)
5'-GTGTCTGCAGTGATGGTCACCCTGCCCTGGAAC-3'

5' VH (80):
(SEQ ID NO: 68)
5'-GCACTGCCTACATGGAGCTCTCCAGC-3'

5' VH (93):
(SEQ ID NO: 69)
5'-GTGTACTTCTGCGCCAGATCCCTGAATATG-3'

The sequences of the 20- to 25-bp-long end primers that were used for DNA amplification of the desired $V_L$ and $V_H$ genes were as follows:

5' VL: 5'-GC*AAGCTT*CCACCATGGATA-3' (SEQ ID NO: 70)
5' VH: 5'-CTA*GAATTC*CACCATGGAGTGGTCC-3' (SEQ ID NO: 71)
3' VH: 5'-ATGGGCCCGTAGTTTTGGCGC-3' (SEQ ID NO: 72)

Each of the 5' primers carries a restriction endonuclease site (HindIII for $V_L$ and EcoRI for $V_H$), followed by the Kozak consensus sequence and a sequence encoding the N-terminus of the signal peptide. The 3' $V_L$ end primer (either primer SEQ ID NO: 6 or 8) contains a unique SacII site located 10 bp downstream from the start of the human κ C region, while the 3' $V_H$ primer carries a unique ApaI site located 17 bp downstream from the start of the human $C_H1$ domain.

DNA mutagenesis and sequencing: All PCR amplifications were carried out in EasyStart™ 50 tubes (Molecular Bio-Products, San Diego, Calif.) in a final volume of 50 μl of PCR buffer (20 mM Tris-HCl (pH 8.4), 50 mM KCl) containing 2 mM $MgCl_2$, 200 μM of dNTPs, 2.5 units of the high-fidelity copy PfuTurbo DNA polymerase (Stratagene Cloning Systems, La Jolla, Calif.), 0.1% Triton X-100, 25 pmoles each of the appropriate 5' and 3' primers, and 100 ng of the DNA template. Initial denaturation at 95° C. for 7 minutes was followed by 30 cycles of denaturation at 95° C. for 30 seconds, annealing at 55° C. for 30 seconds and extension at 72° C. for 1 minute, and a final primer extension step at 72° C. for 10 minutes.

The $V_L$ and $V_H$ genes of the framework variants of V10 were generated using a two-step PCR method as described by Landt et al. (*Gene* 96:125-128, 1990). The first PCR was carried out using a mutagenic oligomer as one of the two primers to incorporate a desired change, while the mutated product of the first PCR was used as one of the primers for the second PCR. After an initial denaturation at 95° C. for 7 minutes, 30 cycles of denaturation (95° C., 1 minute), primer annealing (45° C., 1 minute) and extension (72° C., 2 minutes) were followed by a final extension for 10 minutes at 72° C. When the mutations were located in the middle of the $V_L$ or $V_H$ gene, an overlap extension PCR was used to incorporate the alterations (Higuchi et al., *Nucleic Acids Res* 16:7351-7367, 1988; Ho et al., *Gene* 77:51-59, 1989). Two separate PCRs were performed to amplify two halves of the complete gene. The resulting PCR fragments were annealed and amplified using the appropriate 5' and 3' end primers.

Expression vector and generation of expression constructs: Prior to cloning into expression vectors, the synthesized $V_L$ or $V_H$ genes were sequenced using the ABI PRISM™ dRhodamine terminator cycle sequencing kit (Perkin Elmer Applied Biosystems, Foster City, Calif.). The mammalian expression vector pDCMdhfr (FIG. 1) was used for the co-expression of the Ig L and H chains in Chinese hamster ovary (CHO) cells. The pDCMdhfr vector was constructed by joining the NruI and PvuI double-digested DNA fragments of the vectors, kc-dhfrΔE-S (Ryu et al., *Hum Antibodies Hybridomas* 7:113-122, 1996) and pDCM, a construct derived from pcDNA3 (Invitrogen, Carlsbad, Calif.). pDCMdhfr contains cloning sites for the two target genes, each downstream from an enhancer-promoter complex of the immediate early genes of human CMV. The plasmid also includes a dhfr expression unit driven by an enhancer-deficient SV40 early promoter, and a neomycin resistance gene for drug selection of transfectants.

To generate a pDCMdhfr expression construct of the genes encoding the L and H chains of the V10 parental Ab, a construct containing the L chain was first generated (FIG. 1A). This was done by sequential digestion of the pre-existing construct pBScHuCC49V5 (Tamura et al., *J Immunol* 164: 1432-1441, 2000) with EcoRI, mung bean nuclease, and HindIII. V5 encodes the light chain gene of the parental mAb V10. It was followed by the ligation of the resulting V5 DNA fragment into the pDCMdhfr vector that has been pre-treated with ApaI, mung bean nuclease, and HindIII. A DNA fragment encoding the H chain gene of the mAb V10 was generated by ClaI digestion, addition of the NotI linker, and EcoRI/NotI digestion of the pre-existing construct pBScHuCC49V8 (Tamura et al., *J Immunol* 164:1432-1441, 2000). The resulting V8 DNA fragment, which encodes the heavy chain of V10, was cloned into the EcoRI/NotI site of the pDCMdhfr vector containing the V10 L chain (FIG. 1B). To generate expression constructs encoding the framework variants of the V10 L chains, the mutated $V_L$ region sequences were exchanged with the $V_L$ sequence of V10 in the pDCMdhfr L chain construct through the HindIII/SacII site, prior to insertion of the H chain gene into the vector. In the pDCMdhfr construct containing both L and H chains, SacII is not a unique site because it is present in the DNA sequence in the C region of the H chain. To generate constructs encoding the H chains of the variants, the PCR-amplified $V_H$ sequences were swapped with the V10 $V_H$ sequence in the pDCMdhfr construct containing both L and H chains, using the unique EcoRI/ApaI site.

Mammalian cell culture and production of recombinant Abs: To develop transfectants expressing V10 and its framework variants, CHOdhfr⁻ cells were transfected with the pDCMdhfr derived expression construct using liposome-mediated DNA transfer (Lipofectamine Plus, Invitrogen) according to the guidelines of the manufacturer. Following transfection, cells were incubated at 37° C. in DMEM/F12 medium overnight, and were then trypsinized and seeded in 96-well plates at $2 \times 10^4$ cells per well in selection medium (alpha MEM, 10% dialyzed fetal bovine serum, 550 μg/ml G418). After 2 weeks of selection, the culture supernatants of the stable transfectants were monitored by ELISA assay and Western blotting.

Purification of recombinant Abs: The highest Ab-producing clones were grown in CHO—S—SFM II serum-free medium (Invitrogen) supplemented with 550 μg/ml G418. Cell culture supernatants were collected and centrifuged at 2,000×g for 10 minutes to remove cellular debris. The supernatant was then loaded on a protein A agarose column (Invitrogen) equilibrated in 20 mM Tris-HCl buffer (pH 7.5). The bound protein was eluted from the column with 0.1 M glycine hydrochloride (pH 2.5) and the pH of the eluted material was immediately adjusted to 7.4 with 1.0 M Tris (pH 8.0). The protein was concentrated using Centricon 30 (Amicon, Beverly, Mass.) and buffer-exchanged in PBS (pH 7.4). The protein concentration was determined using a Bio-Rad protein assay kit (Bio-Rad Laboratories, Hercules, Calif.) based on the method developed by Bradford (Bradford, *Anal Biochem* 72:248-254, 1976). The purity of the Ab preparation was evaluated using the Agilent 2100 Bioanalyzer system (Agilent Technologies, Waldronn, Germany), under reducing and non-reducing conditions, using the Protein 200 LabChip kit (Agilent Technologies).

ELISA: ELISA assays were carried out by coating 96-well polyvinyl microtiter plates with 1 μg/well of bovine submaxillary mucin (BSM) (Sigma-Aldrich, St. Louis, Mo.). The plates were blocked with 5% BSA in PBS for 1 hour at 37° C. and then washed with 1% BSA in PBS. Fifty microliters of culture supernatants were loaded in duplicate wells. After a 1 hour incubation at 37° C. and washing with 1% BSA in PBS, 100 μl of peroxidase-conjugated anti-human IgG (Fcγ-fragment specific) diluted (1:3000) in 1% BSA in PBS was added per well. The plates were incubated for another hour at 37° C. They were washed prior to detection using 100 μl SureBlue™ TMB 1-component peroxidase substrate (KPL, Gaithersburg, Md.). The colorimetric reaction was allowed to proceed for 10 minutes at room temperature in the dark, before it was terminated by the addition of 100 μl of TMB Stop solution (KPL) per well. The absorbance was read at 450 nm.

Empirical comparative analysis of Ag binding via SPR: The Ag reactivity of the Abs was measured by SPR, using a BIAcore X instrument (BIAcore, Piscataway, N.J.). BSM was immobilized on the carboxymethylated dextran CM5 sensor chips by amine coupling (Johnsson et al., *Anal Biochem* 198:268-277, 1991; Schuck et al., *Current Protocols in Protein Science* 2:20.2.1-21, 1999). The dextran layer of the sensor chip was activated by injecting 35 µl of a mixture of N-ethyl-N'-(3 dimethylaminopropyl)carbodiimide hydrochloride and N-hydroxysuccinimide at a flow rate of 5 µl/minute. BSM, diluted in 100 mM sodium acetate buffer (pH 3.0) at a concentration of 100 µg/ml, was injected until a surface of 1000 resonance units (RUs) was obtained. The remaining reactive groups on the surface were blocked by injecting 35 µl of 1 M ethanolamine (pH 8.5). Binding measurements were performed at 25° C. in HBS running buffer (10 mM HEPES (pH 7.4), 150 mM NaCl, 3 mM EDTA and 0.005% Tween 20). Abs (100 µl), in increasing concentrations, were applied sequentially at a flow rate of 5 µl/minute, and the association at each concentration was monitored for 20 minutes. The BSM surface was regenerated, using a 1 minute injection of 6 M guanidine and 0.2 M acetic acid without any loss of the BSM-surface activity.

Competition RIA: The relative Ag-binding affinity of V10 and its variants was determined using a competition RIA as described previously (Tamura et al., *J Immunol* 164:1432-1441, 2000). Twenty-five µl of serial dilutions of the Abs to be tested as well as mCC49 (positive control) and HuIgG (negative control), prepared in 1% BSA in PBS, were added to microtiter plates containing 10 ng of BSM saturated with 5% BSA in PBS. $^{125}$I-labeled mCC49 (100,000 cpm in 25 µl) was then added to each well. After an overnight incubation at 4° C., the plates were washed and the bound radioactivity was counted in a γ-scintillation counter. The relative affinity constants were calculated by a modification of the Scatchard method (Frankel et al., *Mol Immunol* 16:101-106, 1979).

Flow cytometric (FACS) analysis: To evaluate the ability of V10 and its variants to bind to cell-surface TAG-72, a previously described method (Nicolet et al., *Tumour Biol* 18:356-366, 1997) was used for FACS analysis. Jurkat cells ($1\times10^6$), expressing TAG-72, were resuspended in cold $Ca^{++}$ and $Mg^{++}$ free Dulbecco's PBS and incubated with the Abs (V10 or variants) for 30 minutes on ice. A human IgG was used as an isotype control. After one washing cycle, the cell suspension was stained with FITC-conjugated mouse anti-human Ab (PharMingen, San Diego, Calif.) for 30 minutes on ice. After a second washing cycle was performed, the samples were analyzed with a FACScan (Becton Dickinson, Mountain View, Calif.) using CellQuest for Macintosh. Data from the analysis of 10,000 cells were obtained.

Immunoadsorption of patient serum: Stored patients' sera EA and DS, from a Phase I clinical trial (Mulligan et al., *Clin Cancer Res* 1: 1447-1454, 1995) that involved the administration of $^{177}$Lu-labeled mCC49 to patients with advanced adenocarcinoma, were used to assess the sera reactivity of the V10 derived Abs. Sera from patients EA and DS that were found to contain anti-V region Abs to CC49 (Iwahashi et al., *Mol Immunol* 36:1079-1091, 1999) also contained circulating TAG-72 antigen and anti-murine Fc Abs, which could interfere with the binding of the V10 and its variants to the sera anti-V region Abs. To overcome this difficulty, TAG-72 and Abs to murine Fc were removed from the sera by immunoadsorption prior to checking the sera reactivity of V10 and its variants. The procedure for immunoadsorption has been detailed earlier (Iwahashi et al., *Mol Immunol* 36:1079-1091, 1999). Briefly, purified murine CC92, a second-generation mAb that reacts with an epitope of TAG-72 distinct from the one recognized by mCC49 (Koroki et al., *Cancer Res* 50:4872-4879, 1990), was coupled to Reacti-gel (HW65F; Pierce, Rockford, Ill.) (Hearn et al., *J Chromatogr* 185:463-470, 1979). Serum was added to an equivalent volume of the CC92 gel (wet-packed volume) and incubated overnight at 4° C. with end-over-end rotation. The samples were centrifuged at 1000×g for 5 minutes and the supernatant was saved and stored at −20° C.

Sera reactivity: The reactivity of V10 and its variants to anti-V region Abs was determined using a recently developed SPR-based competition assay (Gonzales et al., *J Immunol Methods* 268:197-210, 2002). Competition experiments were performed at 25° C. using a CM5 sensor chip containing HuCC49 in flow cell 1 and rabbit gamma globulin (Bio-Rad), as a reference, in flow cell 2. HuCC49, V10 or its variants were used at different concentrations to compete with the HuCC49 immobilized on the sensor chip for binding to serum anti-V region Abs. Patient's serum with or without the competitor (HuCC49, V10 or its variants) was applied across the sensor surface using a recently developed sample application technique (Abrantes et al., *Anal Chem* 73:2828-2835, 2001). The sample was centered across the sensor surfaces and an oscillatory flow was applied at a rate of 20 µl/minute. After measuring the binding for 1000 seconds, the unbound samples were removed from the surfaces by washing with running buffer using a flow rate of 100 µl/min, and the surfaces were regenerated with a 1 minute injection of 10 mM glycine (pH 2.0). The percent binding at each Ab concentration was calculated as follows:

% binding=[slope of the signal obtained with competitor(serum+Abs)/slope of the signal obtained without competitor(serum only)]×100.

The $IC_{50}$ for each antibody, the concentration required for 50% inhibition of the binding of the serum anti-V region Abs to immobilized HuCC49, was calculated.

Example 2

Design and Generation of the Genes Encoding the V10 Framework Variants

An examination of the $V_L$ sequences of mCC49 and the human Ab LEN reveals that 62 out of the 80 framework residues are identical (Kashmiri et al., *Hybridoma* 14:461-473, 1995). Of the 18 differences, 7 residues were deemed crucial and were grafted onto the human template, along with the CDRs or the SDRs, in generating the humanized Abs HuCC49 and V10, respectively. The $V_H$ sequences of mCC49 and 21/28'CL share 63 identities in 87 framework residues. Out of the 24 differences, 12 were retained as murine in the humanization protocols of CC49. The murine framework residues retained in the V domains of the HuCC49 and V10 Abs are at positions 5, 19, 21, 43, 78, 100 and 106 in $V_L$, and at positions 12, 20, 38, 40, 48, 66, 67, 69, 71, 80, 91 and 93 in $V_H$ (numbering convention of Kabat et al. (Kabat et al., *Sequence of Proteins of Immunological Interests*, 5$^{th}$ ed., p. NIH Publication No. 91-3242, U.S. Department of Health and Human Services, National Institutes of Health, Bethesda, Md., 1991)). Analysis of the known three-dimensional structures of Ab:Ag complexes available in the PDB database (Abola et al., *Methods Enzymol* 277:556-571, 1997) reveals that the residues at the positions enumerated above are probably important in keeping the overall structure of the combining site, because they are either buried or implicated in the direct interaction with the Ag (Amit et al., *Science* 233:747-753, 1986; Colman et al., *Nature* 326:358-363, 1987; Fischmann et al., *J Biol Chem* 266:12915-12920, 1991; Padlan et al., *Proc Natl Acad Sci USA* 86:5938-5942, 1989; Sheriff et al., *Proc Natl Acad Sci USA* 84:8075-8079, 1987; Tulip et al.,

*J Mol Biol* 227:122-148, 1992), contact with CDRs (Chothia et al., *J Mol Biol* 196:901-917, 1987; Chothia et al., *Nature* 342:877-883, 1989; Tramontano et al., *J Mol Biol* 215:175-182, 1990), or in the $V_L/V_H$ interaction (Padlan, *Mol Immunol* 31:169-217, 1994). The crucial nature of these murine framework residues, however, has not been validated in the case of CC49. It is probable that some of the framework residues deemed crucial to maintain Ag reactivity of the other Abs are not that essential for the Ag:Ab interaction of CC49. Several variants of mAb V10 were designed to test the indispensability of some of the murine framework residues for the Ag-binding reactivity of CC49 by replacing them with the corresponding residues in the human Abs.

Figure 2:
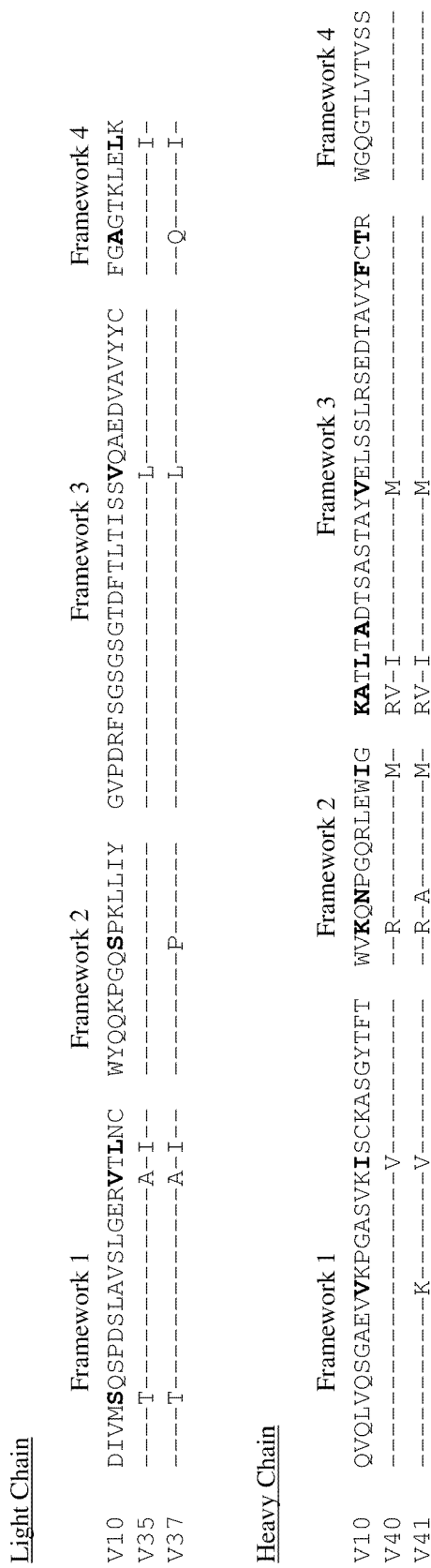
FIG. 2 shows the amino acid sequences of the framework variants of HuCC49V10. The complete amino acid sequence of all the frameworks of the humanized Ab HuCC49V10 is given in the top row of each of the light (SEQ ID NOs: 1-4) and heavy chain (SEQ ID NOs: 5-8) panels. Letters in bold indicate the murine framework residues that were retained in the HuCC49V10. Dashes indicate residues that are identical among V10, V35, and V37, or V10, V40, and V41.
Figure 3:
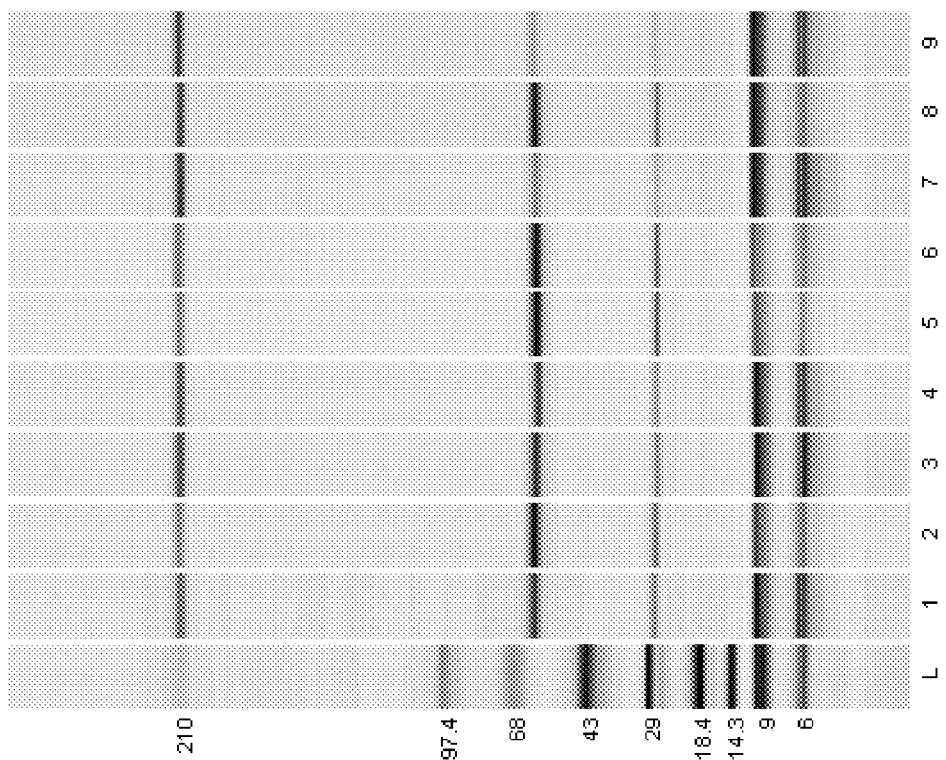
FIG. 3 is a digital image of an analysis of the purified recombinant Abs using the Agilent Bioanalyzer system under reducing conditions. Lane L, molecular weight (m.w.) markers; Lane 1, V10; Lane 2, V35; Lane 3, V37; Lane 4, V40; Lane 5, V41; Lane 6, V47; Lane 7, V48; Lane 8, V58; Lane 9, V59. Sizes of the m.w. markers are given in the column at the left. Three peaks are present in all lanes corresponding to the lower maker (6 kDa), system peak (9 kDa) and upper marker (210 kDa).

Genes encoding the $V_L$ and $V_H$ domains of the variants were generated by primer-induced mutagenesis, using the pBScHuCC49V5 and pBScHuCC49V8 constructs (Tamura et al., *J Immunol* 164:1432-1441, 2000), which contain the L and H chains of V10, respectively, as the templates. The V region sequences were synthesized either by a dual step PCR or an overlap extension PCR, as described in Materials and Methods. Each of the V regions of the L and H chains was generated by the primer-induced mutation, inserted into the pDCMdhfr expression cassette, as described in Materials and Methods, and subsequently sequenced. V35 was generated by replacing the murine $V_L$ framework residues 5, 19, 21, 78 and 106 of V10 with the corresponding residues of the human Ab LEN. V37 contains two additional changes at positions 43 and 100, making all the framework residues in the $V_L$ of this variant human. To generate V40, the $V_H$ framework residues 20, 38, 48, 66, 67, 69 and 80 of the V10 were replaced with the corresponding residues of the human Ab 21/28'CL. In addition to all the mutations present in V40, mutations at positions 12 and 40 were also included in V41. In this $V_H$ variant, only three murine residues located at positions 71, 91 and 93 of the murine Ab have been retained. The amino acid sequences of the $V_L$ and $V_H$ frameworks of the parental V10 and the mutated variants are shown in FIG. 2. Variants containing different combinations of the parental and variant L and H chains are listed in Table II.

most of the V10 variants, like those of V10 transfectomas, were positive. The highest producing clone of each construct was cultured under identical conditions, and the secreted Abs were purified from the culture supernatants. The purity of the Ab preparations was verified by the Agilent 2100 Bioanalyzer system, using a Protein 200 LabChip. The profiles of all recombinant Abs were identical under reducing and non-reducing conditions. Under reducing conditions (FIG. 3), all Abs yielded two protein bands of approximately 24-27 kDa and 60 kDa. These molecular masses are in conformity with those of the Ig L and H chains, respectively.

Example 4

Binding of V10 Framework Variants to TAG-72-Positive BSM

To assess the binding reactivity of the framework variants to the TAG-72$^+$ BSM, an SPR-based assay was carried out using a sensor chip with BSM immobilized on its surface. Increasing concentrations of different Abs were allowed to interact with the BSM surface for 20 minutes. Responses could be measured after the binding of the antibody to the surface BSM reaches equilibrium, but a steady state could not be attained for most of the samples, especially at the higher concentrations. Nonetheless, the magnitude of the response signals could provide a measure of the binding interaction of different Abs to the BSM surface.

Figure 4:
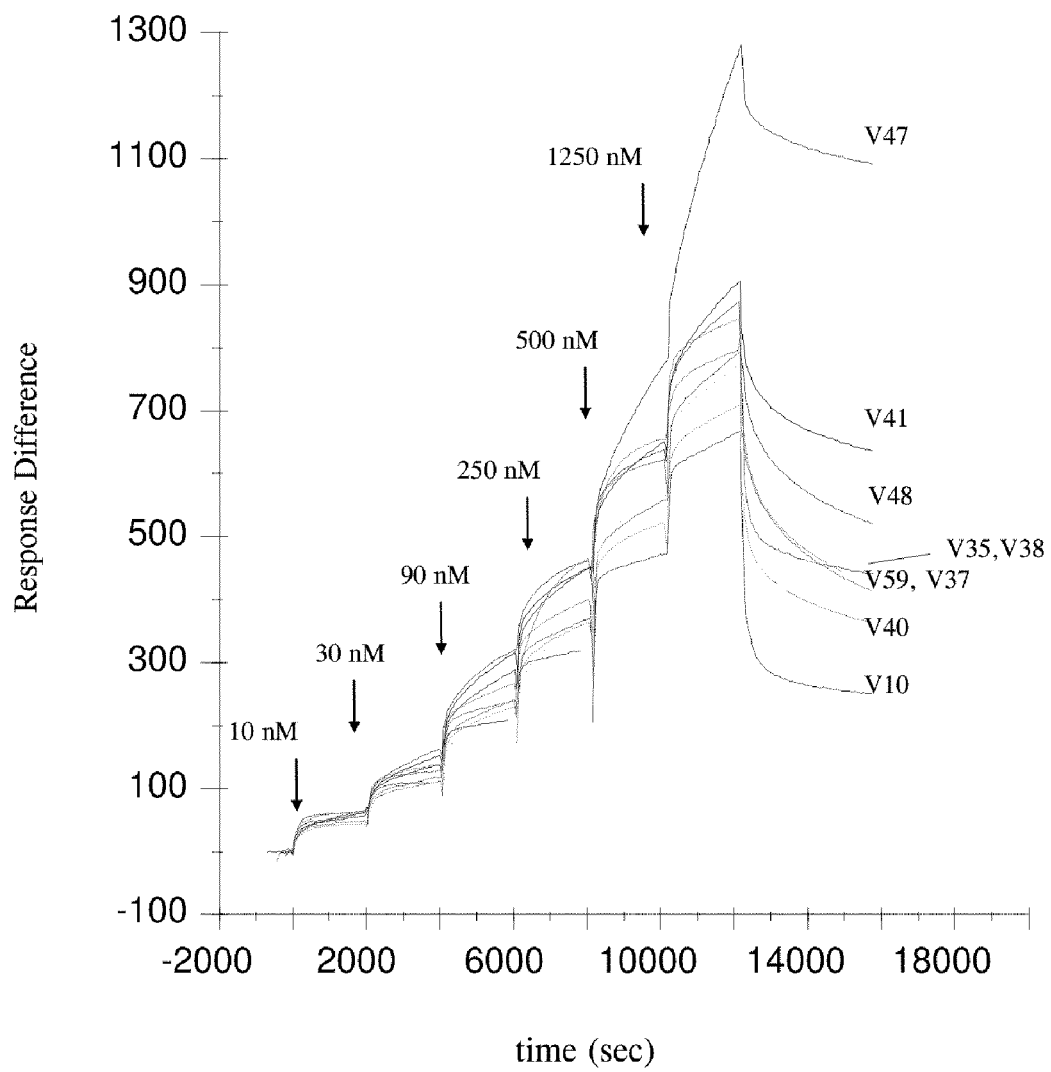
FIG. 4 is a set of binding sensorgrams of V10 and V10-derived framework variants to BSM immobilized onto the surface of a CM5 sensor chip. Binding was measured using a Biacore X system, as described in Materials and Methods, at Ab concentrations of 10, 30, 90, 250, 500 and 1250 nM.

Results from the binding measurements revealed that different framework variants generate distinctly different profiles of binding to the surface BSM. An examination of the binding profiles suggests that all the framework variants have retained their reactivity to BSM (FIG. 4). Higher response signals by some of the variants than that generated by V10 may suggest that some variants have higher affinity for the Ag than that of the parental Ab. When a sensor chip immobilized with anti-human Fcγ specific Ab was used, the binding profiles of all the framework variants to the anti-human Fcγ sensor chip were not different from each other. Thus, the

TABLE II

Residue positions substituted in the HuCC49V10 framework variants

| Variant | Light Chain | Heavy Chain |
| --- | --- | --- |
| V10 (parent) | None | None |
| V35 | 5, 19, 21, 78, 106 | None |
| V37 | 5, 19, 21, 43, 78, 100, 106 | None |
| V40 | None | 20, 38, 48, 66, 67, 69, 80 |
| V41 | None | 12, 20, 38, 40, 48, 66, 67, 69, 80 |
| V47 | 5, 19, 21, 78, 106 | 20, 38, 48, 66, 67, 69, 80 |
| V48 | 5, 19, 21, 43, 78, 100, 106 | 20, 38, 48, 66, 67, 69, 80 |
| V58 | 5, 19, 21, 78, 106 | 12, 20, 38, 40, 48, 66, 67, 69, 80 |
| V59 | 5, 19, 21, 43, 78, 100, 106 | 12, 20, 38, 40, 48, 66, 67, 69, 80 |

Example 3

Expression of V10 Variants in CHOdhfr$^-$ Cells

The expression constructs of the genes encoding the H and L chains of the parental mAb V10 and its framework variants were introduced into CHOdhfr$^-$ cells. The supernatants harvested from the G418 resistant transfectants were assayed for Ig production by ELISA and Western blot analysis as described in Materials and Methods. Most of the transfectants, like those generated by the control constructs of V10, were found to be positive for Ig production. When the culture supernatants were assayed for their reactivity to TAG-72, differences in the signals generated by different variants against BSM are due to their binding reactivity to BSM, and not because of differences in their protein concentrations.

The complexity of the surface-binding reaction of whole antibodies, attributed mainly to their bivalency, precludes a detailed interpretation of the time-course of binding, as is frequently applied to SPR biosensor data (Schuck, *Biophys Biomol Struct* 26:541-566, 1997). In addition, the multiplicity of Ab binding sites on the BSM surface [disaccharide and trisaccharide structural epitopes (Hanisch et al., *Biol Chem Hoppe Seyler* 370:21-26, 1989)) complicated the analysis of the biosensor data. Therefore, it is not possible to calculate the exact relative affinity constants of the variants from their binding profiles generated by the SPR-based assay. Nevertheless, a simple comparison of the binding signals at defined concentrations for each antibody gave a semi-quantitative measure of its surface-binding reactivity.

Figure 5:
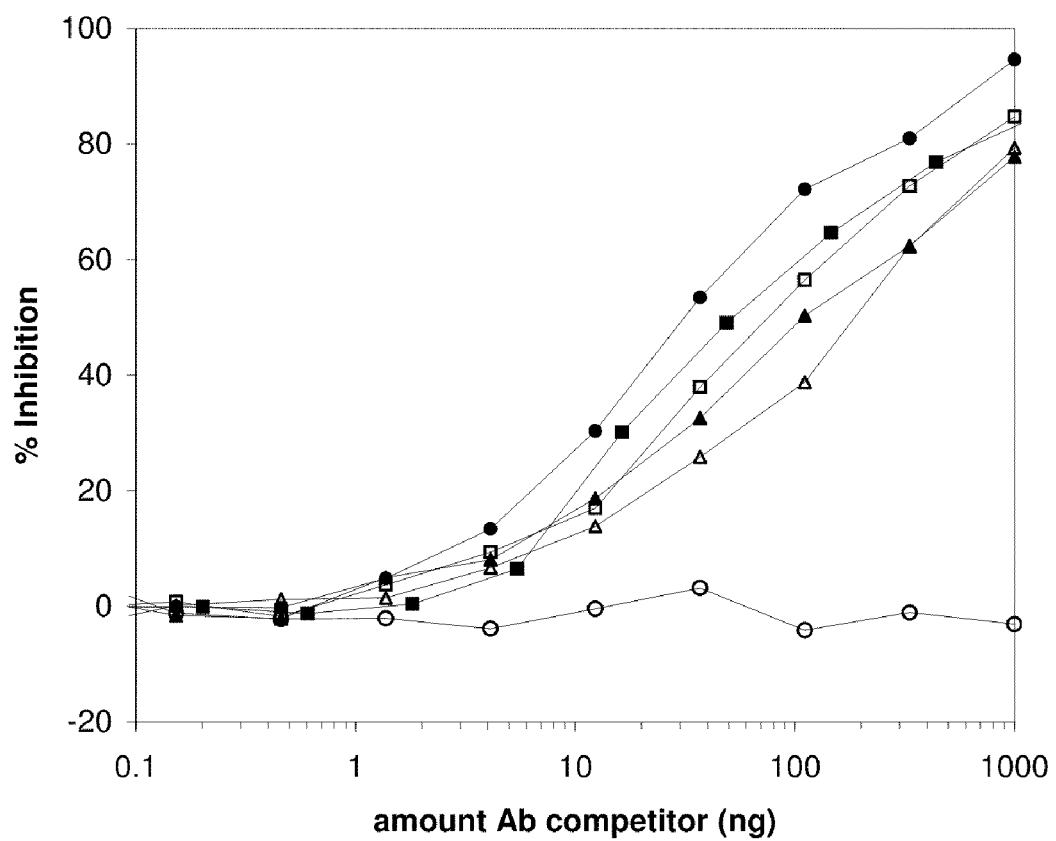
FIG. 5 is a graph of a competition RIA of V10-derived framework Abs. Increasing concentrations of Abs mCC49 (●), HuCC49 (■), V10 (▲), V47 (△), V59 (□), and HuIgG (○) were used to compete for the binding of $^{125}$I-labeled mCC49 to 10 ng of BSM coated in each well.

To determine the relative affinity constants of the variants, competition RIA was carried out. Only two of the variants, V59 and V47, were compared to the parental Ab V10. These two variants were selected, because the latter generated the highest response profile in the SPR-based assay, while the former carries the largest number of human residues in its frameworks. Competition RIA, which included mCC49 and HuCC49 as positive controls and an irrelevant human IgG as a negative control, was performed as described in Example 1. Serial dilutions of unlabeled Abs were used to compete with the binding of $^{125}$I-mCC49 to BSM. Results presented in FIG. 5 show that the competition profile of the V47 variant is shifted slightly to the right, while that of V59 slightly to the left of the V10 profile. Compared to 110 ng of V10 Ab, Briefly, 217 ng of V47 and 85 ng of V59 (compared to 110 ng of V10) were required for 50% inhibition of the binding of $^{125}$I-mCC49 to BSM (Table III).

TABLE III

Relative binding affinities of framework variants via competition RIA.

| Antibody Name | Amount of Ab Required for 50% Inhibition (ng) | Ka (relative affinity constant) $\times 10^8$ M$^{-1}$ |
|---|---|---|
| mCC49 | 33 | 1.98 |
| HuCC49 | 55 | 1.16 |
| V10 | 110 | 0.59 |
| V47 | 217 | 0.32 |
| V59 | 85 | 1.08 |

These results are in conformity with the values of the relative affinity constants ($K_a$) of V10, V47 and V59 that were found to be $0.59 \times 10^8$ M$^{-1}$, $0.32 \times 10^8$ M$^{-1}$ and $1.08 \times 10^8$ M$^{-1}$, respectively (Table III). The affinity constants were calculated from the linear parts of the competition curves shown in FIG. 5. The relative affinity constants of mCC49 and HuCC49 were found to be $1.98 \times 10^8$ M$^{-1}$ and $1.16 \times 10^8$ M$^{-1}$, respectively.

The competition RIA results seem to be at variance with the data in FIG. 4 in which V47 shows the highest binding response to BSM using the SPR-based assay. It should be noted, however, that the competition RIA was carried out at low concentrations of Abs (highest concentration used was 135 nM) to reflect the binding of the Abs to the high-affinity binding site in BSM. The higher binding signals of V47 by SPR were evident only at high Ab concentrations (500 and 1250 nM), which reflect the binding of V47 to the low-affinity binding sites in BSM.

Example 5

Binding of V10 Variants to Cell Surface TAG-72

Figure 6:
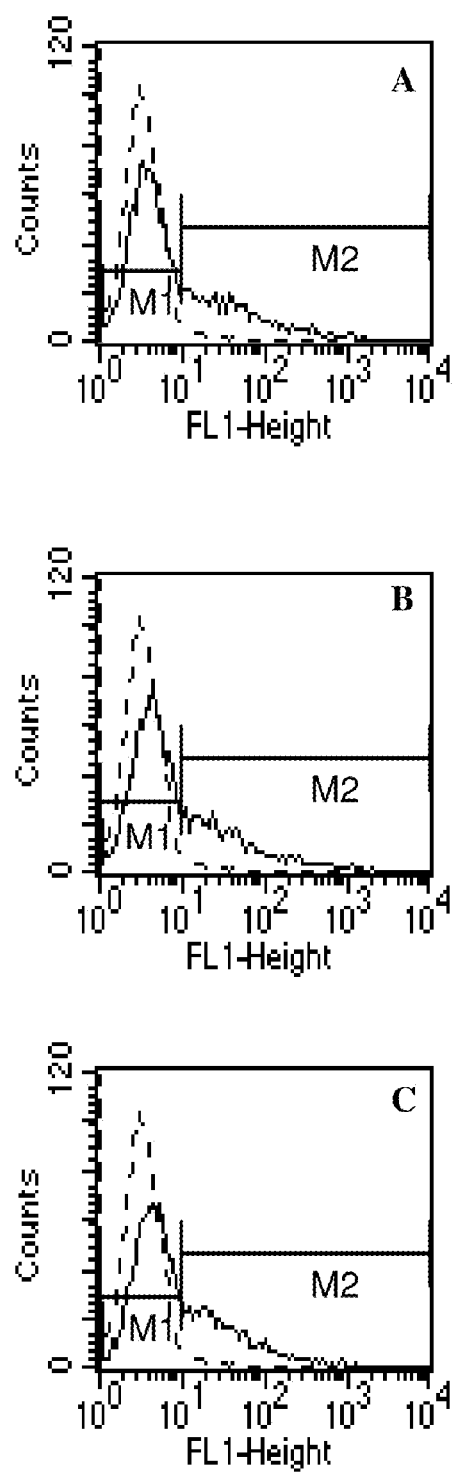
FIGS. 6A-C are plots of flow cytometric analysis of the binding of V10 and its variants to cells expressing cell surface TAG-72. Binding profiles of 0.5 µg of V10 (FIG. 6A), V47 (FIG. 6B) and V59 (FIG. 6C) to Jurkat cells expressing TAG-72 on its cell surface. Binding of an irrelevant mAb, human IgG (dashed line) is shown in each panel and represents less than 1% of the cell population.

Flow cytometric analysis was used to measure the binding of V10, V47 and V59 to the TAG-72 expressed on the cell surface of Jurkat cells (Nicolet et al., *Tumour Biol* 18:356-366, 1997). When 0.5 µg of each Ab was used, no significant differences were found in the mean fluorescence intensity, or in the percentage of Jurkat cells that were reactive with V10 and its framework variants (FIG. 6). V59 and V47 showed 29.0% and 27.6% of gated cells and the mean fluorescence intensities of 49.8 and 56.8, respectively, compared with V10, which showed 25.8% of gated cells and a mean fluorescence intensity of 62.9. Thus, the binding of the two framework variants to cells displaying TAG-72 on their cell surfaces was not significantly different from that of the parental Ab V10.

Example 6

Reactivity of V10 and its Framework Variants to Patients' Sera

Figure 7:
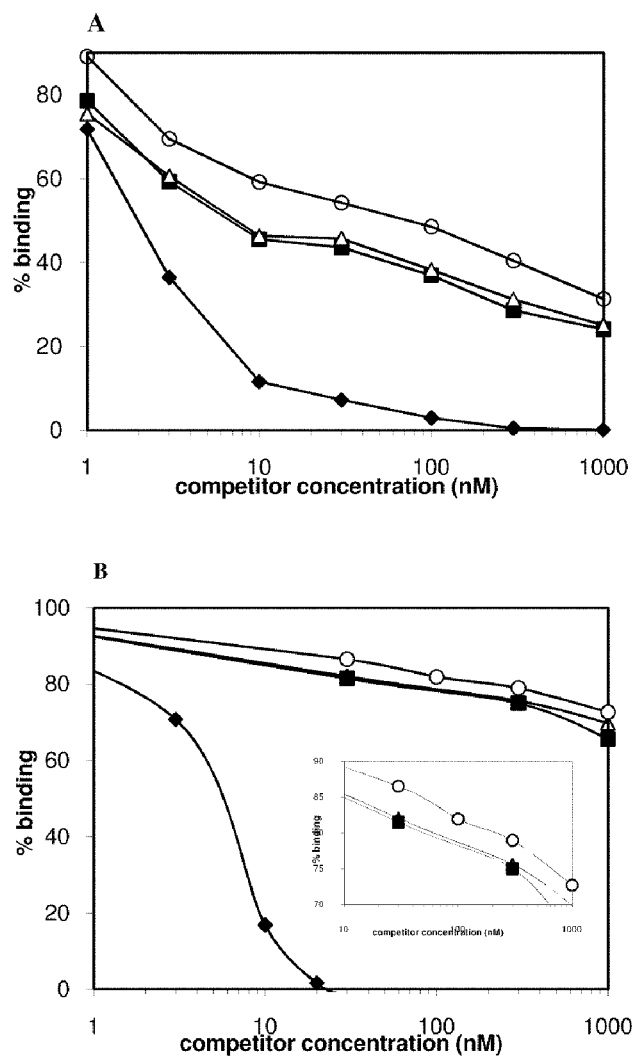
FIGS. 7A-B are two plots showing sera reactivity, by SPR, of V10 and its framework variants. Increasing concentrations of HuCC49 (♦), V10 (■), V47 (△), and V59 (○) mAbs were used to compete with the anti-V region Abs to CC49 present in the sera of patients EA (FIG. 7A) and DS (FIG. 7B) for binding to HuCC49 immobilized on a sensor chip. Percent binding of the sera to immobilized HuCC49 was calculated from the sensorgrams and plotted as a function of the concentration of the competitor.

To assess the potential immunogenicity of V47 and V59, relative to V10, the Abs were evaluated for their in vitro reactivity to sera from adenocarcinoma patients who were treated with $^{177}$Lu-mCC49 in a phase I clinical trial (Mulligan et al., *Clin Cancer Res* 1:1447-1454, 1995). As described in Example 1, any circulating TAG-72 and anti-murine Fc Abs were removed from the sera by immunoadsorption with mCC92, a murine Ab of the same isotype as that of mCC49, that reacts with an epitope of TAG-72 different from the one recognized by mCC49. Previous studies have shown that the pre-adsorbed sera from patients EA and DS contain anti-V region Abs to mCC49 (Gonzales et al., *J Immunol Methods* 268:197-210, 2002; Iwahashi et al., *Mol Immunol* 36:1079-1091, 1999; Tamura et al., *J Immunol* 164:1432-1441, 2000). Sera reactivity of HuCC49, V10 and its variants was determined by their ability to compete with HuCC49 immobilized on a sensor chip for binding to the mCC49 anti-V region Abs present in the patient's serum. The IC$_{50}$ value, the concentration of the competitor Ab required for 50% inhibition of the binding of immobilized HuCC49 to the patient's serum, was calculated by plotting the percent binding as a function of competitor concentration. A higher IC$_{50}$ value indicates a decreased reactivity to the serum, suggesting reduced potential immunogenicity of the Abs in patients. FIG. 7 shows the competition profiles generated by HuCC49, V10 and its variants when they were used to compete with the HuCC49 immobilized on the sensor chip for binding to the anti-V region Abs present in the sera of patients EA (FIG. 7A) and DS (FIG. 7B). The pattern of the competition profiles for the two patients' sera was similar. The variant V47 shows the same reactivity as V10, whereas V59 demonstrates a weaker reactivity to the sera, as reflected by the shift in the competition curves to the right. The IC$_{50}$ value of V59 for the serum EA is about 10-fold and 35-fold higher than that of V10 and HuCC49, respectively (Table IV).

TABLE IV

Concentrations of competitor antibody required for half-maximal inhibition (IC$_{50}$) of binding of patients' sera to HuCC49 immobilized on the sensor chip

| Competitor Antibody | Patient EA (nM) | Patient DS (nM) |
|---|---|---|
| HuCC49 | 2.2 | 6.0 |
| V10 | 7.7 | >1000 |
| V47 | 8.2 | >1000 |
| V59 | 82.5 | >1000 |

For the serum DS, the binding of HuCC49 to the serum anti-V region Abs was only minimally inhibited by V10 and V59. The IC$_{50}$ values could not be determined because even 1000 nM of the variants failed to achieve more than 30% inhibition of the binding of sera antibodies to the HuCC49 immobilized on the sensor chip. Still, the competition profile of V59 is shifted slightly to the right of V10. Compared to 80 nM of V10 or V47, approximately 200 nM of V59 is required for 20% inhibition of the binding of the sera anti-V region Abs to HuCC49 immobilized on the sensor chip (FIG. 7B, Inset).

This corresponds to a 2.5-fold decrease in the reactivity of V59 to the DS serum, compared to V10. Compared to HuCC49, which caused 20% binding inhibition at 2 nM concentration, the inhibition by V59 is 100-fold less.

The two most important and often contrary aims in humanizing an Ab are (a) retention of its Ag-binding property and (b) reducing its immunogenicity in patients. For the retention of ligand-binding property, the functional conformation of the Ab-combining site must be preserved, which requires maintenance of the CDRs and their interaction with each other and with the rest of the structure of the antibody-combining site. Successful humanization of an Ab, therefore, depends on selecting the most appropriate human templates based on sequence identity and optimization of the acceptor frameworks to retain those murine framework residues that may be crucial in maintaining the structural integrity of the combining site. Unfortunately, optimization of the frameworks increases the risk of making the Ab immunogenic in patients. The more murine framework residues are retained in a humanized Ab, the more immunogenic it is likely to be. Framework residues are considered crucial when they (i) are involved in direct interaction with the Ag (Amit et al., *Science* 233:747-753, 1986; Colman et al., *Nature* 326:358-363, 1987; Fischmann et al., *J Biol Chem* 266:12915-12920, 1991; Padlan et al., *Proc Natl Acad Sci USA* 86:5938-5942, 1989; Sheriff et al., *Proc Natl Acad Sci USA* 84:8075-8079, 1987; Tulip et al., *J Mol Biol* 227:122-148, 1992), (ii) contact the CDRs affecting the structure of their loops and, consequently, the Ag-binding site (Chothia et al., *J Mol Biol* 196:901-917, 1987; Chothia et al., *Nature* 342:877-883, 1989; Tramontano et al., *J Mol Biol* 215:175-182, 1990), (iii) are involved in $V_L/V_H$ interaction (Padlan, *Mol Immunol* 31:169-217, 1994), and (iv) are buried and influence the overall structure of the combining site. In the absence of a three-dimensional structure of the Ab:Ag complex, as in the case of mCC49, selecting the crucial framework residues to be retained in the humanized Ab is based on the analysis of the known crystal structures of other Ab:Ag complexes that are available in the PDB database (Abola et al., *Methods Enzymol* 277:556-571, 1997). As shown herein, data obtained by studying the effect of site-specific mutations on the ligand-binding property of a particular Ab provides definite information as to which framework residues are absolutely essential for its Ag-binding property (compared to the information obtained from the PDB database). This approach helps to exclude all those murine framework residues from the humanized Ab that are dispensable for the Ag-binding activity and led to the development of antibodies that elicited only a minimal immune response in patients.

The humanized Ab, V10, was generated by grafting only the SDRs of CC49 onto the $V_L$ and $V_H$ frameworks of human Abs LEN and 21/28'CL, respectively, while retaining those murine framework residues that were presumed essential, according to the PDB database, for its Ag-binding activity. The dispensability of some of the murine framework residues that were retained in V10 was tested in the experiments disclosed herein by replacing them with their counterparts in human templates and evaluating the Ag-binding activity of the resulting variants.

Framework variants of V10 were designed to study the effect of several mutations (substitutions of human for the murine residues) concurrently, instead of generating mutants containing individual changes. Abs containing different combinations of $V_L$ and $V_H$ variants were also generated. ELISA and SPR assays show that all of the framework variants retain reactivity to TAG-72 positive BSM. Competition RIA further shows that the Ag-binding affinity of the combination variant V59 was comparable to that of V10. The variant V59, the most humanized variant of V10, contains only three murine residues in its $V_H$ frameworks, compared with 19 murine residues in the $V_L$ and $V_H$ frameworks of V10. This translates to an increase in the human residue content to 91.2% in V59 from 84.2% in V10. These results lead to the conclusion that the $V_L$ frameworks of CC49 can be replaced fully with those of the human Ab LEN without any loss of activity; only positions 94 and 96 in LCDR3 have been retained as murine in the L chain of V59. Furthermore, the human substitutions in the $V_H$ at positions 12, 20, 38, 40, 48, 66, 67, 69 and 80 do not adversely affect the Ag-binding affinity of the Ab.

Whether the V59 variant displays reduced potential to evoke anti-V region response in patients as opposed to the CDR-grafted HuCC49 or V10 was assessed by comparing their reactivity to the sera from adenocarcinoma cancer patients who were administered $^{177}$Lu-CC49 in a Phase I clinical trial (Mulligan et al., *Clin Cancer Res* 1:1447-1454, 1995). The sera were shown to carry anti-V region antibodies to CC49 (Gonzales et al., *J Immunol Methods* 268:197-210, 2002; Iwahashi et al., *Mol Immunol* 36:1079-1091, 1999; Tamura et al., *J Immunol* 164:1432-1441, 2000). The results show that V59, compared with V10, was less reactive to two patients' sera, EA and DS.

Thus, the humanization of the V10 Ab has been augmented by replacing murine framework residues, initially deemed crucial in maintaining the combining site structure, with the corresponding human residues. Judicious manipulation of framework residues, disclosed herein, has led to the optimization of the humanization of an Ab and has been used to enhance its biological properties. The experiments disclosed herein show that, for the first time, manipulation of framework residues can decrease the sera immune reactivity of Abs.

Example 7

Clinical Studies

A non-blinded, single-arm pilot "phase I" evaluation of $^{125}$I radiolabeled are V47, V48, V58, and/or V59 monoclonal antibody (mAb) in the intraoperative detection of disease in human subjects undergoing surgery for metastatic colorectal cancer is performed. During the surgical procedure, detection or localization of the antibody in primary or recurrent tumor is performed using the Neoprobe® hand-held gamma-detecting probe. The primary objective is to determine the time interval from antibody injection to surgery that minimizes the time interval from injection to surgery while insuring that no more than ⅓ (one-third) of patients fail to demonstrate tumor localization.

Prior to surgery, patients are injected with 2 mCi of $^{125}$I radiolabeled to 1 mg of mAb by intravenous injection. Beginning two days prior to injection of the antibody, patients are given a saturated solution of potassium iodide (SSKI) 10 drops daily to block thyroid uptake of the radioiodinated mAb. Thyroid blocking is continued for two weeks postinjection.

To determine the optimum time interval from injection to surgery a modified 'standard method' 3 by 3 phase I design is used. A cohort of three patients initially undergoes surgery at 3 days (72 hours) following injection. If all three patients localize the metastatic tumor, the time interval is reduced to two days (48 hours) between antibody injection and surgery. If one of three patients fails to localize, an additional three patients are treated at that time interval. If two or more of six patients fail to localize, it is determined if failure to localize is due to either high background counts obscuring tumor-bound antibody or low overall counts reflecting rapid clearance of both circulating and bound antibody. If the failure is due to high counts, the next cohort of three patients is treated at an interval from injection to surgery increased to four days (96 hours). If failure is due to low overall counts, the next cohort has their interval reduced to two days (48 hours). This three patient cohort is evaluated as the previous cohort. If all three patients localize, the interval is reduced to one day (24 hours) from injection to surgery. Patients do not have their interval from injection to surgery reduced to less than one day (24 hours) or greater than seven days (168 hours).

The surgeon initially explores the abdomen using traditional techniques (visually and manually) to determine the presence or absence of tumor. Following exploration, the surgeon uses the gamma-detecting probe device to obtain triplicate, 2-second counts of non-lymphatic tumor(s) identified by traditional techniques. A biopsy of at least one tumor identified by traditional surgical techniques is obtained if possible. The gamma-detecting probe device is used to obtain counts of the tumor margin. All counts are taken in triplicate.

Abdominal exploration is carried out to assess areas of abnormal radioactive uptake using a gamma detecting probe. Attempts are made to procure as much tumor tissue and tumor associated antigen lymphatic tissue as possible for sampling. Biopsies of the liver, lymph nodes and peritoneum (particularly the momentum) are obtained when appropriate. A final status of residual radioactivity is recorded at the completion of the surgical procedure.

Pharmacokinetic parameters are determined by noninvasive daily precordial counts obtained using a Neoprobe® 1000 probe for a period of seven days following injection of the radiolabeled monoclonal antibody. Quantitative 24-hour urine specimens are collected for 72 hours following injection. This initial study requires not fewer than 12 patients or more than 30 patients.

Data is analyzed to determine the optimal time from injection to surgery based on tumor localization. Safety data on adverse events associated with the mAb administration and surgical procedure are reported. The optimum time interval is then recommended for further study.

It will be apparent that the precise details of the methods or compositions described may be varied or modified without departing from the spirit of the described invention. We claim all such modifications and variations that fall within the scope and spirit of the claims below.

The invention claimed is:

1. An isolated nucleic acid encoding a humanized anti-TAG-72 CC49 monoclonal antibody, wherein the humanized anti-TAG-72 CC49 monoclonal antibody comprises a light chain comprising a light chain Complementarity Determining Region (L-CDR)1, a L-CDR2, a L-CDR3, and light chain framework regions 1-4 from HuCC49V10, a heavy chain comprising a heavy chain Complementarity Determining Region (H-CDR)1, a H-CDR2, a H-CDR3, and heavy chain framework regions 1-4 from HuCC49V10, wherein the residues at positions 5, 19 and 21 of SEQ ID NO: 1 (light chain framework region 1) are replaced with threonine, alanine, and isoleucine, respectively, and the residue at position 9 of SEQ ID NO: 4 (light chain framework region 4) is replaced with isoleucine, and wherein the residue at position 20 of SEQ ID NO: 5 (heavy chain framework region 1) is replaced with valine, the residues at positions 3 and 13 of SEQ ID NO: 6 (heavy chain framework region 2) are replaced with arginine and methionine, respectively, and the residues at positions 1, 2, 4, and 15 of SEQ ID NO: 7 (heavy chain framework region 3) are replaced with arginine, valine, isoleucine, and methionine, respectively;

wherein the humanized CC49 antibody retains binding affinity for TAG-72 and has reduced immunogenicity, as compared to the HuCC49V10 antibody encoded by the nucleic acid sequences deposited as ATCC Accession No. PTA-5416.

2. A vector comprising a promoter operably linked to the nucleic acid of claim 1.

3. A host cell transformed with the vector of claim 2.

4. The host cell of claim 3, wherein the cell is a eukaryotic cell.

5. The isolated nucleic acid of claim 1, wherein the humanized anti-TAG-72 CC49 monoclonal antibody further comprises a proline at position 9 of SEQ ID NO: 2 (light chain framework region 2).

6. The isolated nucleic acid of claim 1, wherein the humanized anti-TAG-72 CC49 monoclonal antibody further comprises a leucine at position 22 of SEQ ID NO: 3 (light chain framework region 3).

7. The isolated nucleic acid of claim 1, wherein the humanized anti-TAG-72 CC49 monoclonal antibody further comprises a glutamine at position 3 of SEQ ID NO: 4.

8. The isolated nucleic acid of claim 1, wherein the humanized anti-TAG-72 CC49 monoclonal antibody further comprises a lysine at position 12 of SEQ ID NO: 5.

9. The isolated nucleic acid of claim 1, wherein the humanized anti-TAG-72 CC49 monoclonal antibody further comprises a valine at position 20 of SEQ ID NO: 5.

10. The isolated nucleic acid of claim 1, wherein the humanized anti-TAG-72 CC49 monoclonal antibody light chain framework region further comprises proline at position 9 of SEQ ID NO: 2 (light chain framework region 2), leucine at position 22 of SEQ ID NO: 3 (light chain framework region 3), glutamine at position 3 of SEQ ID NO: 4, and lysine at position 12 of SEQ ID NO: 5.

11. The isolated nucleic acid of claim 1, wherein the humanized anti-TAG-72 CC49 monoclonal antibody L-CDR1 comprises an amino acid sequence set forth as SEQ ID NO: 9, L-CDR2 comprises an amino acid sequence set forth as SEQ ID NO: 10, and L-CDR3 comprises an amino acid sequence set forth as SEQ ID NO: 11.

12. The isolated nucleic acid of claim 1, wherein the humanized anti-TAG-72 CC49 monoclonal antibody H-CDR1 comprises an amino acid sequence set forth as SEQ ID NO: 12, H-CDR2 comprises an amino acid sequence set forth as SEQ ID NO: 13, and H-CDR3 comprises an amino acid sequence set forth as SEQ ID NO: 14.

13. The isolated nucleic acid of claim 1, wherein the encoded humanized anti-TAG-72 CC49 monoclonal antibody is conjugated to a detectable label.

14. The isolated nucleic acid of claim 1, wherein the encoded humanized anti-TAG-72 CC49 monoclonal antibody is conjugated to an effector molecule.

* * * * *